US009168076B2

(12) United States Patent
Patty et al.

(10) Patent No.: US 9,168,076 B2
(45) Date of Patent: Oct. 27, 2015

(54) BONE COMPRESSION SCREW

(71) Applicant: Bridging Medical, Inc., Kaysville, UT (US)

(72) Inventors: Robert Michael Patty, Abilene, TX (US); Cameron Field, Highlands Ranch, CO (US); Andrew Enke, Salt Lake City, UT (US); Daniel Robert Patty, Draper, UT (US)

(73) Assignee: BRIDGING MEDICAL, LLC, Tooele, UT (US)

( * ) Notice: Subject to any disclaimer, the term of this patent is extended or adjusted under 35 U.S.C. 154(b) by 56 days.

(21) Appl. No.: 13/793,865

(22) Filed: Mar. 11, 2013

(65) Prior Publication Data

US 2014/0257412 A1 Sep. 11, 2014

(51) Int. Cl.

| | |
|---|---|
| ***A61B 17/86*** | (2006.01) |
| ***A61B 17/84*** | (2006.01) |
| *A61B 17/68* | (2006.01) |
| *A61B 17/82* | (2006.01) |

(52) U.S. Cl.

CPC ........... *A61B 17/8615* (2013.01); *A61B 17/842* (2013.01); *A61B 17/864* (2013.01); *A61B 17/8605* (2013.01); *A61B 17/8665* (2013.01); *A61B 17/8685* (2013.01); *A61B 17/8695* (2013.01); *A61B 17/82* (2013.01); *A61B 17/844* (2013.01); *A61B 17/861* (2013.01); *A61B 17/8635* (2013.01); *A61B 2017/681* (2013.01); *A61B 2017/867* (2013.01); *Y10T 29/49881* (2015.01)

(58) Field of Classification Search

CPC ............. A61B 17/8615; A61B 17/864; A61B 17/842; A61B 17/8685

USPC ...................... 606/70, 71, 246–279, 300–331

See application file for complete search history.

(56) References Cited

U.S. PATENT DOCUMENTS

| | | | |
|---|---|---|---|
| 4,131,031 | A | 12/1978 | Erikson |
| 4,204,566 | A | 5/1980 | Kirrish |
| 4,958,970 | A | 9/1990 | Rose |
| 4,959,064 | A | 9/1990 | Engelhardt |
| 5,482,463 | A | 1/1996 | Wilson |
| 5,791,850 | A | 8/1998 | Mundt |
| 6,648,903 | B1 | 11/2003 | Pierson, III |
| 6,656,184 | B1 | 12/2003 | White |

(Continued)

FOREIGN PATENT DOCUMENTS

| | | |
|---|---|---|
| CH | 669898 A5 | 4/1989 |
| DE | 19741087 | 4/1999 |

(Continued)

*Primary Examiner* — Christopher Beccia

(74) *Attorney, Agent, or Firm* — Maywood IP Law; G. Jo Hays; David W. Meibos

(57) ABSTRACT

A system for orthopedic repair of bones, the system may include a compression screw. The screw may include a blunt tip on one end with tapped threads to allow for greater bone fixation uniform across a threaded portion of the screw. The screw may also include springs, which may be Belleville washers, which provide appropriate compression and tension and prevent excessive loosening of the screw after surgery. The springs allow the screw to retract without losing pressure on the fracture site. The system may be minimally invasive for multiple fractures on a single bone such as calcaneal fractures, and stabilizing long bone fractures without bone plates.

20 Claims, 26 Drawing Sheets

334 332 314 330 338 314 328 324 310 316 326 322 320 336 312 318

(56) References Cited

U.S. PATENT DOCUMENTS

| | | | |
|---|---|---|---|
| 6,712,855 | B2 | 3/2004 | Martin |
| 6,860,691 | B2 | 3/2005 | Unsworth |
| 7,141,073 | B2 | 11/2006 | May |
| 7,175,626 | B2 | 2/2007 | Neff |
| 7,621,912 | B2 | 11/2009 | Harms |
| 7,625,395 | B2 | 12/2009 | Mueckter |
| 7,644,930 | B2 | 1/2010 | Pusio |
| 7,833,256 | B2 | 11/2010 | Biedermann |
| 7,842,073 | B2 | 11/2010 | Richelsoph |
| 7,857,832 | B2 | 12/2010 | Culbert |
| 7,942,909 | B2 | 5/2011 | Hammill, Sr. |
| 8,043,333 | B2 | 10/2011 | Frigg |
| 8,048,134 | B2 | 11/2011 | Partin |
| 8,118,849 | B2 | 2/2012 | Wahl |
| 8,328,856 | B1 | 12/2012 | Donahoe |
| 8,337,526 | B2 | 12/2012 | Hestad |
| 2005/0143823 | A1 | 6/2005 | Boyd |
| 2005/0277940 | A1 | 12/2005 | Neff |
| 2006/0282084 | A1 * | 12/2006 | Blier et al. ...................... 606/72 |
| 2007/0270855 | A1 * | 11/2007 | Partin .............................. 606/72 |
| 2008/0147126 | A1 | 6/2008 | Tipirneni et al. |
| 2009/0072456 | A1 | 3/2009 | Barman |
| 2009/0157123 | A1 | 6/2009 | Appenzeller |
| 2009/0255098 | A1 * | 10/2009 | Andberg et al. ................ 24/530 |
| 2010/0268242 | A1 | 10/2010 | Ciccone |
| 2011/0054545 | A1 * | 3/2011 | Champagne et al. ......... 606/301 |
| 2011/0081218 | A1 | 4/2011 | Wang |
| 2011/0144703 | A1 | 6/2011 | Krause |
| 2011/0296668 | A1 | 12/2011 | Emmerich |
| 2011/0313421 | A1 | 12/2011 | Sidebotham |
| 2011/0316191 | A1 | 12/2011 | Di Simone |
| 2011/0319942 | A1 | 12/2011 | Bottlang |
| 2011/0319946 | A1 | 12/2011 | Levy |
| 2012/0003060 | A1 | 1/2012 | Park |
| 2012/0040572 | A1 | 2/2012 | Ooshita |
| 2012/0059428 | A1 | 3/2012 | Epperly |
| 2012/0077150 | A1 | 3/2012 | Goodman |
| 2012/0136356 | A1 | 5/2012 | Doherty |
| 2012/0150181 | A1 | 6/2012 | Dorawa |
| 2012/0150183 | A1 | 6/2012 | Dorawa |
| 2012/0172936 | A1 | 7/2012 | Horrell |
| 2012/0177462 | A1 | 7/2012 | Fritzinger |
| 2012/0191138 | A1 | 7/2012 | Kiester |
| 2012/0223265 | A1 | 9/2012 | Sawada |
| 2012/0226322 | A1 | 9/2012 | Gonzalez-Hernandez |
| 2012/0227695 | A1 | 9/2012 | Bokura |
| 2012/0232597 | A1 | 9/2012 | Sadidha |
| 2012/0251265 | A1 | 10/2012 | Chiu |
| 2012/0330313 | A1 | 12/2012 | Grady |
| 2013/0030465 | A1 | 1/2013 | Hess |

FOREIGN PATENT DOCUMENTS

| | | |
|---|---|---|
| EP | 2527668 | 11/2012 |
| EP | 2538092 | 12/2012 |
| WO | WO2009094629 | 7/2009 |
| WO | WO2009131843 | 10/2009 |
| WO | WO2011051316 | 5/2011 |
| WO | WO2011085272 | 7/2011 |
| WO | WO2012004470 | 1/2012 |
| WO | WO2012079610 | 6/2012 |
| WO | WO2012121705 | 9/2012 |
| WO | WO2012141715 | 10/2012 |

* cited by examiner

BONE COMPRESSION SCREW

CROSS-REFERENCE TO RELATED APPLICATIONS

This application incorporates by reference the following applications in their entirety:

U.S. Patent Application 61/436,160, filed Jan. 25, 2011, entitled BONE SCREW SUSTAINING OSTEOTOMY SITE-STABILIZING COMPRESSIVE FORCE, HOSPITABLE TO OSTEOCLASTIC FORMATION, DYNAMICALLY FOR MONTHS;

U.S. Patent Application 61/479,111, filed Apr. 26, 2011, entitled WIRE-SPRING-CABLES AND A CALCANEOUS SCREW SUSTAINING OSTEOTOMY SITE-STABILIZING COMPRESSIVE FORCE, HOSPITABLE TO OSTEOCLASTIC FORMATION, DYNAMICALLY FOR MONTHS;

U.S. Patent Application 61/485,319, filed May 12, 2011, entitled BONE SCREW AND CABLE CONNECTIONS SUSTAINING OSTEOTOMY SITE-STABILIZING COMPRESSIVE FORCE, HOSPITABLE TO OSTEOCLASTIC FORMATION, DYNAMICALLY FOR MONTHS; and U.S. Patent Application 61/509,004, filed Jul. 18, 2011, entitled MEDICAL APPARATUS.

BACKGROUND

The current disclosure is intended to document further improvements discovered subsequent to submission of provisional patent requests 61/436,160, 61/479,111, 61/485,319 and U.S. 61/509,004 which are all herein incorporated by references. Specifically, modifications disclosed herein include a screw head, of approximately the same size as screw heads in the current art, and transferring load from Belleville style spring washers used as spring elements in bone screws. Bone screws as disclosed herein may be fabricated without self-tapping sharp tips. Installation tapping bits can be used to create gaps on the engaged side of threads, such that in the fully tensioned or compressed state, the screw threads engage the bone more uniformly.

The process of bone fixation includes reapproximating two osseous structures and then holding them together while bone healing takes place. However, within 2 to 24 hours after bone surgery, screws installed to hold fractured bone together loosen significantly.

Often, loose screws will back out of the bone, causing soft tissue irritation. With significant loosening, bone fragments become subject to movement at the fracture site. This movement creates many problems during the healing process including further injury, prolonged healing, nonunion and/or an inappropriate union. These disadvantages often cause recommendation for prolonged non-weight bearing, with pain and with potential for abuse of pain medication. The risks of prolonged non-weight bearing are Deep Vein Thrombosis (DVT's), osteopenia changes, muscle atrophy, joint ankylosis and generalized soft tissue contractures including ligaments, tendons and neurovascular bundles. Depending on the patient and the time frame that non-weight bearing is necessary, some of the aforementioned risks may be non-reversible resulting in chronic morbidity.

Studies have shown that by increasing weight bearing earlier, there is not only a significant reduction in the chronic morbidities listed above, but there is also an increase in functionality and an earlier return to activities. The complications with early weight bearing are the possibility of current hardware failure and fatigue, fracture fragments shifting due to inadequate compression or non-anatomic fixation, and non-unions stemming from either an avascular compromise or micromotion in a seemingly anatomic correction.

The goal of a dynamic compression screw is to allow continued compression that can withstand the forces of early protected weight bearing. This would reduce a substantial amount of physician bills and insurance payouts that can occur due to complications and lost employment.

Screws are routinely installed with the self-tapping, sharp and pointed tip extending beyond the far outside bone surface, into the soft tissues. The disclosed bone hole that is tapped for screw installation, by the conventional screw thread tip, has negative value. The screw tips used to be very dull and not as pointed until the older art and industry standard was altered in an attempt to be self-tapping and thereby speed up the surgical process. Screws now have a bone cutting tip that is usually tricar in nature and very sharp in an attempt to reduce the tapping step. The problem is that the pointed and sharp screws need to be installed with their threads typically extending 2-3 threads beyond the cortex, i.e., into soft tissues. But doing so leaves a sharp knife like object that is exposed outside the bone in soft tissues. This exposed object can create trauma to surrounding tendons, ligaments, bone periosteum and can increase long term post-operative pain.

Finite Element Analysis (FEA) and experimental observations have shown that the highest screw pullout stresses occurred at the upper thread location. Research suggests screws stretch significantly when loaded in tension or shorten when loaded under compression. Either condition accumulates strain toward an end where the maximum strain concentrates stress at the last single screw thread in the bone. The traditional result is the potential for a progressive failure mode wherein a failed thread transfers the highest strain and stress to end threads, which in-turn may overstress bone. Overstressed bone results in microscopic fatigue. The body reacts by resorption causing screw loosening at typical installation loads. The resorption continues down the thread, effectively shearing the screw loose from the bone. Full screw thread to bone engagement is not achieved in the current art. The disclosed device suggests pre-tapping and overdrilling the hole, as mentioned above, and eliminating the sharp cutting tip.

Further, the present device, may also integrate a Belleville washer single spring, stacked spring or reversing stacked spring section into the head of the screws to enable load bearing on the relatively thin but strong cortical bone. This enables the screws to retract and continue to provide the necessary pressure on the bone to hold fracture sites together, secured against movement from internal and external forces, and under compression specific to promoting bone growth. This increases rates at which the bone will heal, decreases soft tissue damage from traditional screw lifting, and prevents additional injury, delayed union, nonunion, and/or inappropriate union. Using these improvements to the current art, fixation can more frequently be done internally, eliminating a source for pin-tract infection risk from external fixation and substantially reducing the complications mentioned above.

Previously engineered dynamic screws are inadequate. Other configurations are simply not structurally capable of producing the tension necessary to hold the bones together at the fracture site, are too rigid to provide sufficient retraction during the loosening phase of healing, or both.

Without these spring screws, animals are often euthanized as the only humane option, and people spend a lot of time in various types of recovery that will no longer be necessary. These new dynamic bone screws enable internal fixation of fractures or osteotomy sites. Internal fixation can improve by closing the fracture zone gap that naturally occurs during healing, and maintain consistent rigid fixation. The proposed screws do not loosen, but relax, stabilizing the joint while allowing earlier movement and weight bearing to stimulate bone growth—reducing net healing time. Traditional head lifting is eliminated, with its attendant soft tissue irritation, screw breakage and the need for surgical removal or retightening. An osteotomy or fracture under the resulting dynamic stabilizing forces, allows early, often immediate motion and weight bearing, as tolerated, resulting in significantly earlier rehabilitation and return to normal activity.

The devices herein disclosed would allow for minimally invasive procedures while allowing patients a quicker return to activity with potential weight bearing immediately after surgery as tolerated, without increasing the risk of nonunion. An earlier return to normal activity and less frustration for patients and their doctors is expected with the device. For a veterinarian, repairing a complex leg fracture on a horse, the ability to achieve weight bearing immediately or very soon after internal fixation surgery can be the difference between life and death for the animal.

The spring screws and cable connections disclosed herein, are mentioned in provisional patents incorporated herein by reference 61/436,160; 61/479,111; 61/485,319; and U.S. 61/509,004; and contain very small, but strong, nested, stiff springs, designed to perform dynamically during internally and externally applied forces and following bone retraction, from healing and from screw bearing-induced bone retraction. The screws and cables are thereby capable of sustained delivery of the level of bone compression sufficient to trigger bone growth and resist internal and external forces while contracting to accommodate the live bone reaction to internal fixation. The devices disclosed herein can retain pressure in a very specific range of bone stresses necessary to trigger bone growth, avoid progressive fissuring from stress concentrations above yield, and avoid stress shielding of the bone.

Creating a blunt screw tip, as suggested in the incorporated provisional applications, can fully engage bone with the full shank of threads. This enables the screw to grab the far cortex after drilling through the near cortex, adhering to the cortical rim while compression takes place. This constitutes a new advancement in the art.

When an osteotomy or fracture is reduced for fixation, whether natural or cut, at the micro scale, the bone-bone interface only actually touches initially at a few small contact points. Screw landings and threads also initially bear on the bone only at small contact points. These small initial contact points, in the fracture zone, below landings and on top of screw threads are locally highly stressed by hardware that is producing compression in the osteotomy. The contact points fissure and are soon resorbed by the body. Early resorption also results in progressive diminution of the fracture gap. Diminution is the gradual (2 to 24 hours) reduction in the physical dimension between cut or fracture surfaces during the natural healing process. Tension in rigid hardware (used to create compression in an osteotomy or natural fracture) is reduced by diminution of the cut or natural fracture gap. An orthopedic screw, installed through a fractured joint, stretches a few microns when it is tightened to a specified torque. When diminution occurs in the joint, the stretching relaxes and the installed force of tension in the screw is correspondingly relaxed. Further relaxation of hardware may result from continued fissuring and resorption of small contact points under landings and on top of threads bearing on bone. This fissuring diminution may continue until a more uniformly distributed stress at bone to bone contact points and on head & thread to bone contact areas achieve a net bone yield stress levels of 60 $N/mm^2$ or below, seating the joint and hardware. With conventional hardware, tension in the screw drops quickly, because the screws are stiff.

By integrating a spring-like section into screws and cables, proposed herein, the hardware will retract and continue to provide the necessary pressure on the bone for diminution and seating to complete while continuing to hold fracture sites together under compression. Internal fixation, using such spring loaded hardware, is secured against movement from internal and external forces, and can be optimized to sustain compression specific to promoting bone growth. It is disclosed that this may enable bone bridging, increasing rates at which the bone will heal, decrease soft tissue damage from traditional screw lifting, and prevent additional injury, delayed union, nonunion, and/or malunion. Using such dynamic hardware, fixation can more frequently be done internally, eliminating external fixation sources for pin-tract infection.

It is herein postulated that achieving a more uniformly distributed stress distribution between threads and bone could achieve a net higher pullout value and quickly seat the hardware at bone yield stress levels below 60 $N/mm^2$, above which natural fissuring and resorption would otherwise continue to occur. By limiting bone fissuring and resorption on active bearing thread surfaces, less spring action will be required to maintain a tight, functional screw.

The device more efficiently utilizes the cross section of the purchased bone, and delivers a significantly higher level of compression, reliably sustained within the desired range to promote bone growth throughout the natural bone retraction that occurs during the healing process following fixation which the current art fails to accomplish. Existing competitive screws have sharp, pointed tips whereas the disclosed device may not include sharp, pointed tips.

Installation tapping bits can create gradually tapered gaps in the active engagement zone, e.g., on tension screws, above threads, such that in the fully tensioned state, the screw threads engage the bone more uniformly. By matching fully stressed screw dimensions with the pre-threaded gap used to install it, the threads more uniformly engage the bone, yielding a substantially increased pullout value.

SUMMARY

A system may include a body with a shaft between proximal and distal ends. The proximal portion may include a base and a head with springs between them. The base and head may have larger diameters than the shaft itself and the base may have a bone engaging surface to engage a portion of a bone. In addition both the base and head may have spring engaging portions to interact or engage the springs between them. The system may include some or all of the following features of threads extending radially from the distal portion and a blunt distal tip. Other features may include bores or apertures passing centrally through each of the base, the head and the springs. The apertures may allow the components of the head, base and springs to slidably engage the shaft. The springs may be Belleville washers and there may be one or multiple Belleville washers and all the Belleville washers may face a single direction. The head may also include threads to engage a proximal end of the body, the head also including a polygonal shape to engage an insertion or installation tool.

Another embodiment of the system may include first and second portions each comprising shafts with proximal and distal portions. Each of the first and second portions may also include a head and a base. The first portion head and base may include springs between them with spring engaging surfaces on both the base and head. The second portion may include an intermediate component and springs between the base and the intermediate component with both the base of the second portion and the intermediate component including spring engaging surfaces. The head of the second portion may be positioned proximate to the intermediate portion. In this alternate embodiment, there may be a rod engaged with both the first and second portions and positioned between them. Other features of the alternate system may include threads on intermediate component and the bases include a central aperture that may be threaded and engages threads on the first and second shafts respectively. The springs that are spaced between the components referenced may be a Belleville washer or multiple Belleville washers and those washers may all face the same direction or they may face different directions. The heads in both the first and second portions may be hexagonal in shape and may engage first and second proximal ends of the first and second shafts respectively.

One method of assembling the devices disclosed above is to slide a base onto a shaft, or screw from the proximal end of the shaft because the distal end includes a threaded portion with threads extending radially from the shaft that are too large for the aperture of the base to pass over. Springs may then slide onto the shaft, after the base, and slide freely along the shaft in a manner similar to the base, the springs also including an aperture large enough to slide from a proximal end, but not the distal end of the shaft. Finally positioning a head proximal the springs and the base and either engaging the shaft through threading, press fit, snap fit or other means. The springs include at least one Belleville washer which engages the base and the head. The distal end of the shaft may include recessed threads to engage the head in a threading manner listed above to prevent the springs and base from being removed from the shaft. Although press-fitting, welding or snap-fitting, with the absence of threads, may also be another means to prevent withdrawal of the base and springs from the shaft.

The disclosed device proposes configuring spring washers into screws and cable connections to deliver the compressive force necessary to promote bone growth while retracting to close the gap(s) and continue compressive force, with flexibility to resist internal and external forces that may otherwise cause movement in the joint. The disclosed spring configurations also avoid unbalanced internal stiffness problems that could otherwise result in progressive or fatigue failure under cyclic loading. Additionally a radio frequency controlled strain gauge may be used and installed in the screw shanks and cable anchors to record the actual current strain in the screw or cable during and following installation and transmit it by radio frequency transmission to an external reader. Power may be provided by magnetic induction from an external source. Thus, spring-screw or wire-cable tension induced bone compression can be accurately set during installation and monitored throughout the healing process which can take months. Thereby early detection of compression outside the acceptable range and adjustment, correction or protection is feasible to prevent delayed healing and avoid complications.

By micro-adjusting tapped thread spacing to match a fully stressed condition of screw and bone, with freeboard, i.e., gap where necessary for installation; a more uniform distribution of bone stress can be achieved and thereby higher pullout loads, while avoiding yield stress concentrations of 60 $N/mm^2$ or above.

BRIEF DESCRIPTION OF THE DRAWINGS

While exemplary embodiments of the present technology have been shown and described in detail below, it will be clear to the person skilled in the art that changes and modifications may be made without departing from its scope. As such, that which is set forth in the following description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the technology described herein can be included within the scope of the present technology.

DETAILED DESCRIPTION

Figure 1:
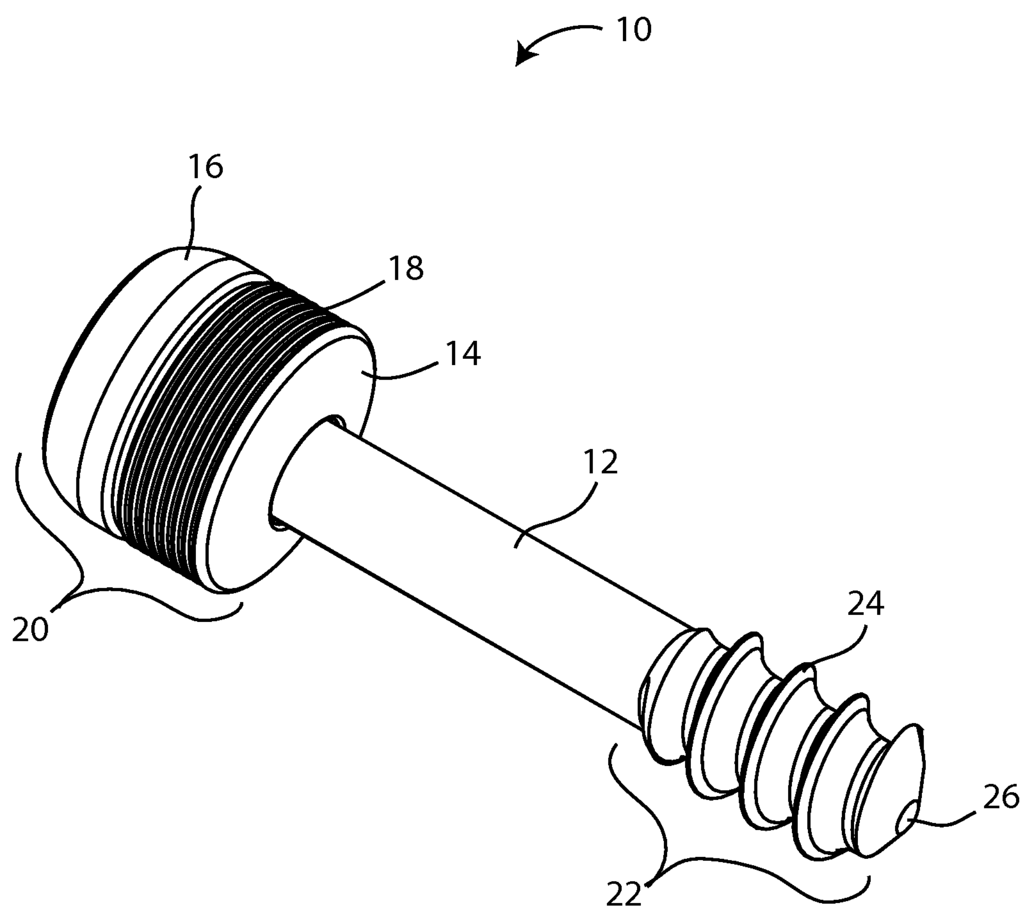
FIG. 1 is perspective view of a system including a shaft with a base a head and springs.

Micro movements occasioned by loose screws and twisted wires cause many problems including delayed non-union or pseudoarthrosis—formation of a false joint caused by the failure of the bones to fuse.

It is contemplated that hardware loosening is largely due to necrosis, fissuring and resorption of fracture zone contact points and at hardware contact points. When a bone fractures, the surface of the fracture dies, which may be 15 microns deep on each side due to lack of blood. Cut osteotomy may result in greater damage to the cut surface due to the blade action and thereby more joint bone necrosis. When a joint bone is reduced for fixation, whether natural or cut, at the micro scale, the joint bone only actually touches initially at a few small contact points. Screw landings and threads also initially bear on bone only at small contact points.

These small initial contact points, in the fracture zone and below landings and on top of screw threads, are locally highly stressed by hardware that is producing compression in the bone. The contact points fissure and are soon resorbed by the body. This early resorption results in progressive diminution of the fracture gap. Diminution is the gradual (2 to 24 hours) reduction in the physical dimension between fracture surfaces. Tension in rigid hardware (used to create compression in a cut or natural osteotomy) is often reduced by diminution of a fracture gap. An orthopedic screw, installed through the fractured zone of the bone or through an osteotomy, stretches a few micros when it is tightened to a specified torque. When diminution occurs in the zone of bone healing, the stretching relaxes and the installed force of tension in the screw is correspondingly relaxed. Further relaxation of hardware may result from fissuring and resorption of small contact points under landings and on top of threads bearing on bone.

The proposed device, described herein, integrates a spring-like section into screws and cables such that the hardware will retract and continue to provide the necessary pressure on the bone to hold fracture sites together. Internal fixation, using such spring loaded hardware, is secured against movement from internal and external forces, and can be optimized to sustain compression specific to promoting bone growth. This sustained compression may enable bone bridging, increased rates at which the bone will heal, decrease soft tissue damage from traditional screw lifting, and prevent additional injury, delayed union, nonunion, and/or inappropriate union. Furthermore, the current device, using such dynamic hardware, fixation can more frequently be done internally, eliminating external fixation sources for pin-tract infection.

One embodiment of the current device proposes configuring spring washers into screws and cable connections to deliver the compressive force necessary to promote bone growth while retracting to close gaps and continue compressive force with flexibility to resist internal and external forces that may otherwise cause movement in the joint. Some of the current spring configurations also avoid unbalanced internal stiffness problems that could otherwise result in progressive or fatigue failure under cyclic loading. As previously disclosed, a radio frequency controlled strain gauge may be installed in the screw shanks and cable anchors to record the actual current strain in the screw or cable during and following installation and transmit it by radio frequency transmission to an external reader for those reasons previously disclosed.

Referring to FIG. 1, a system 10, which may be a compression screw, includes a shaft 12, or shank, a base 14, head 16 and springs 18, or washers or spring washers. The screw 10 may come pre-assembled or may be screwed and pinged, press fitted or welded into place as a single piece permanently assembled to prevent disassembly during installation, use or removal.

Figure 2:
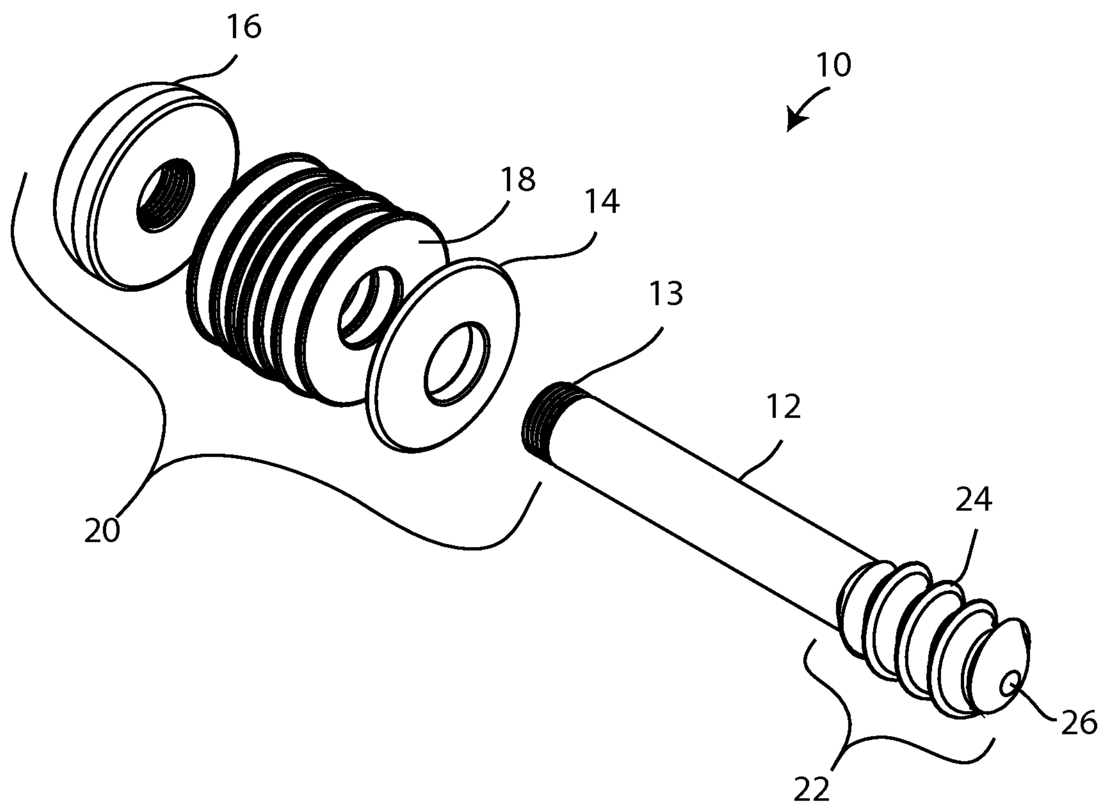
FIG. 2 is an exploded perspective view of the system of FIG. 1.
Figure 3:
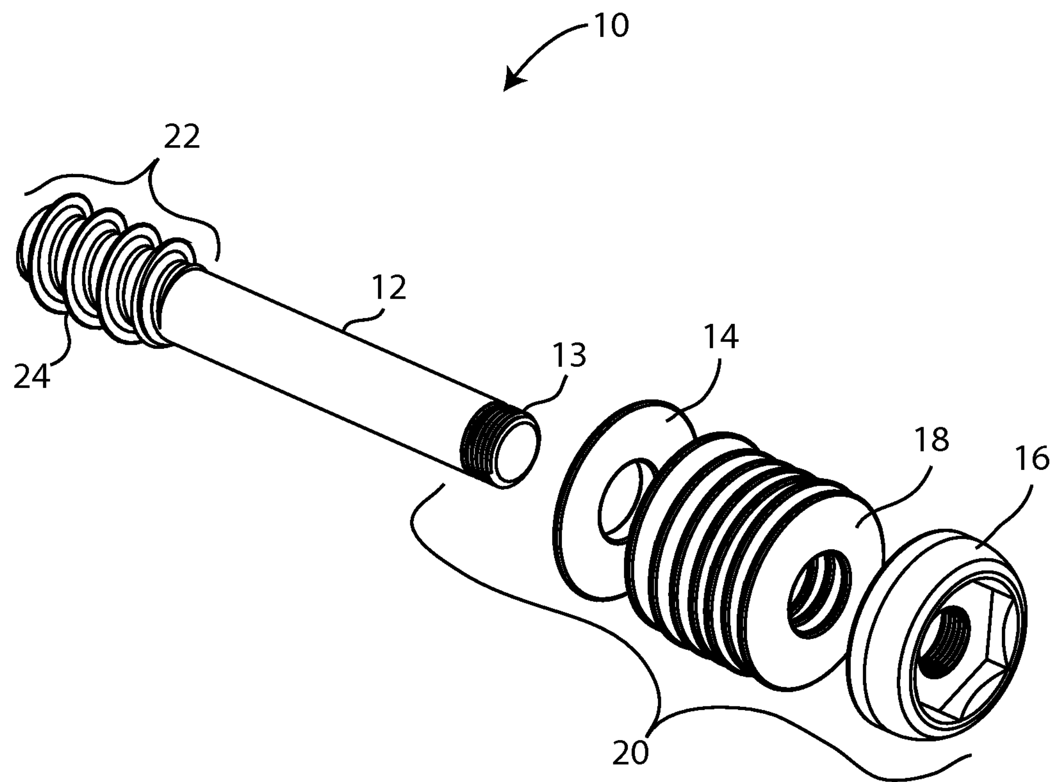
FIG. 3 is an alternate exploded perspective view of the system of FIG. 1.

Referring to FIGS. 2 and 3, the screw 10 includes a proximal portion 20 which may include the base 14, the head 16, the springs 18 and a proximal end of the shaft 12. The screw 10 also includes a distal portion 22 which mainly comprises a distal end of the shaft 12. The distal portion 22 may include threads 24 which may be typical (bone screw threads. A distal tip 26 of the shaft 12 may be a blunt end.

The shaft 12 of the screw 10 comprises a longitudinally extending cylindrical body with a longitudinal axis. A proximal end 13 of the shaft 12 may comprise threads configured to engage the head 16, or screw head. The base 14, or head base, may slidably engage the shaft 12 by sliding onto the shaft 12 at the proximal end 13. The springs 18 may also slidably engage the shaft 12 by sliding onto the shaft 12 at the proximal end 13. The head 16 may threadably engage the shaft by threading onto the proximal end 13, of the shaft. The shaft 12 may include a non-threaded portion between the distal portion 22 and the proximal end 13. The shaft 12 may also include a lip or shoulder between the proximal end 13 and the distal portion 22. The lip or shoulder may be configured to engage the base 14 to retain the base 14, springs 18 and head 16 near the proximal end 13 of the shaft 12. However, a lip is not necessary and the base 14 and springs 18 may slide along the entire shaft from the proximal end 13 to the distal portion 22.

Figure 4:
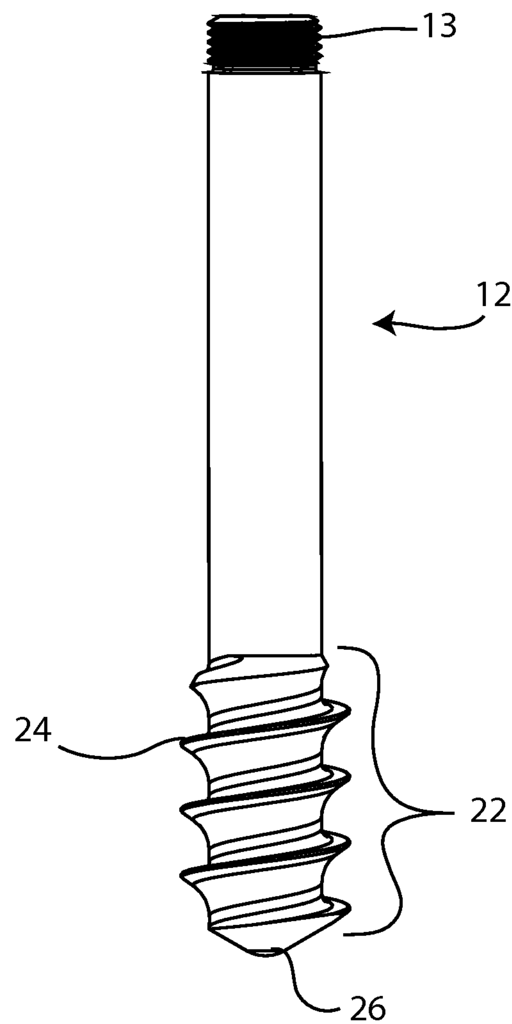
FIG. 4 is a side view of the shaft of the of FIG. 1.

Referring to FIG. 4, the shaft 12 is illustrated by itself with the threaded distal portion 22 with the distal tip 26 and the threaded proximal end 13. The non-threaded portion between the distal portion 22 and the proximal end 13 may be smooth. The threads 24 may extend radially and helically from the distal portion 22 of the body of the shaft 12 with threads 24 having a greater diameter than the main body of the shaft 12. The distal tip 26 may be a blunt end to provide greater fixation within a bone tunnel or with the cortex of a bone with the help of threads 24 may be full sized threads which may also aid in successfully grabbing and maintaining placement while the screw 10 is compressed. The proximal end 13 may be smooth or tapered or may include ridges or barbs to engage the head, or base, of the proximal portion 24.

The proximal end 13 may be polygonal in shape instead of threaded and may be a hexagon. A hexagonal shape may require a complementary fit in the head 16 with a hexagonally shaped aperture in the head 16 to allow for a press or snap fit. While a hexagonal shape may be ideal and provide for an Allen wrench type of insertion and tightening method it will be appreciated that any polygonal shape may work.

Figure 5:
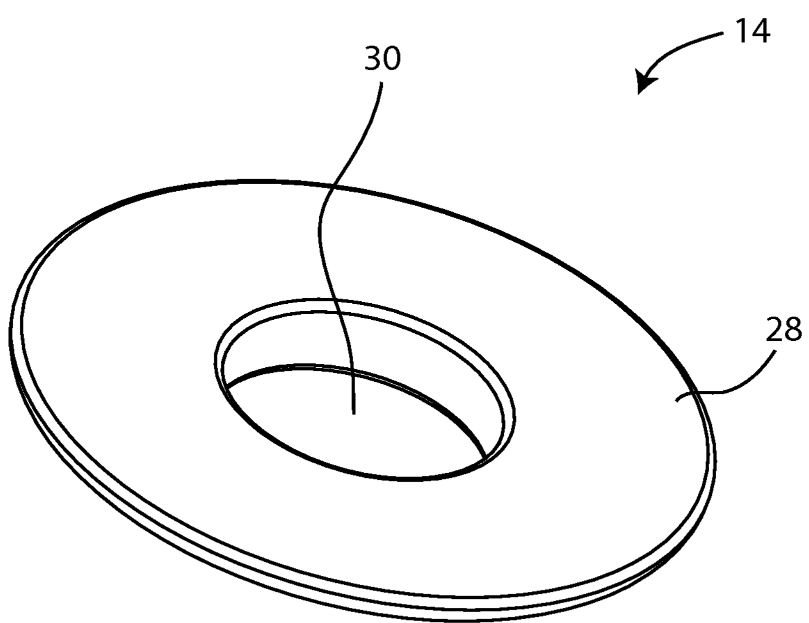
FIG. 5 is a perspective view of the base of FIG. 1.

Referring to FIG. 5, the base 14 may be substantially disc shaped with a first spring engagement surface 28, or upper surface, wherein the upper surface 28 may be flat to allow the springs 18 to rest on the upper surface 28. The base may also include a first aperture 30, which may be central to the base 14, which may be substantially cylindrical, may extend entirely through the body of the base and configured to receive the proximal end 13 of the shaft 12. The first aperture 30 may slidably receive the proximal end 13 or may threadably receive the proximal end 13 as well.

Figure 6:
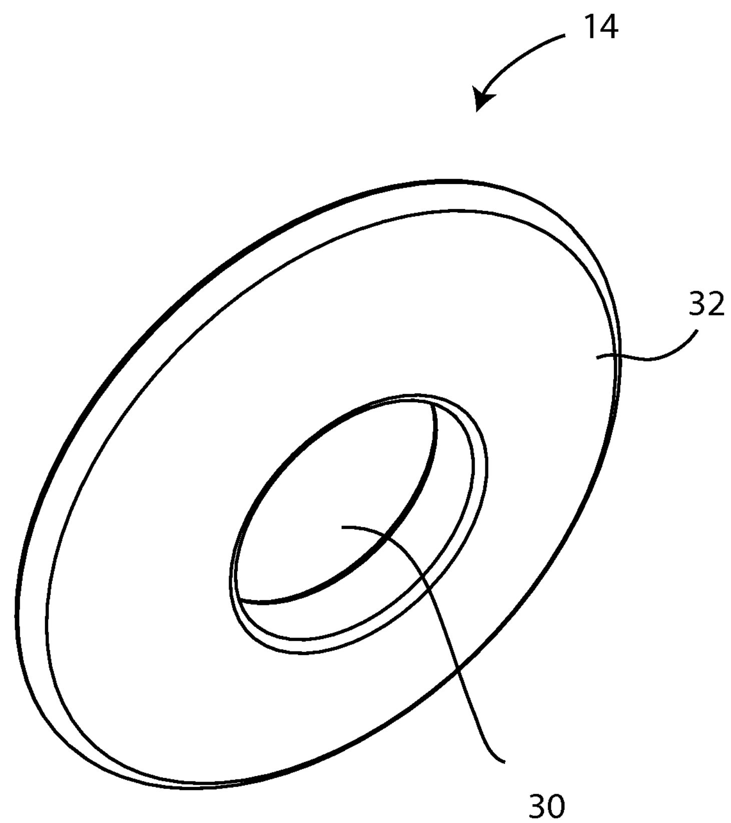
FIG. 6 is an alternate perspective view of the base of FIG. 5.
Figure 7:
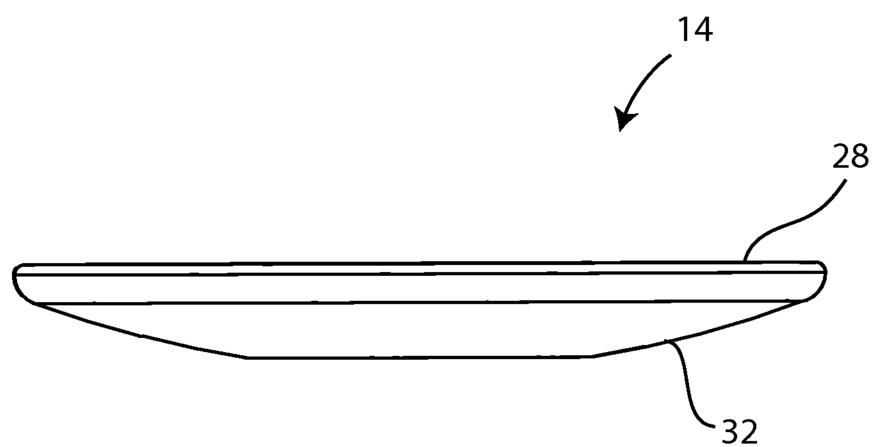
FIG. 7 is a cross sectional side view of the base of FIG. 5.

Referring to FIGS. 6-7, the base 14 also includes a bone engagement surface 32, or bottom surface, wherein the bottom surface 32 may be somewhat convex in shape. The bottom surface 32 is configured to engage the cortex of a bone. A portion of the bottom surface 32 nearest the aperture 30 may engage the lip of the shaft 12 as previously mentioned herein. The aperture 30 when engaged with the shaft 12 may be coaxial with the longitudinal axis of the shaft 12. The base 14 diameter may be larger than the diameter of the shaft; however the diameter of the first aperture 30 may be smaller than the diameter of the non-threaded portion extending between the proximal end 13 and the distal portion 22, thus allowing the base 14 to fit over the proximal end 13 but resting on the lip or shoulder, as previously disclosed, between the distal end and the portion extending between the proximal end 13 and distal portion 22.

Figure 8:
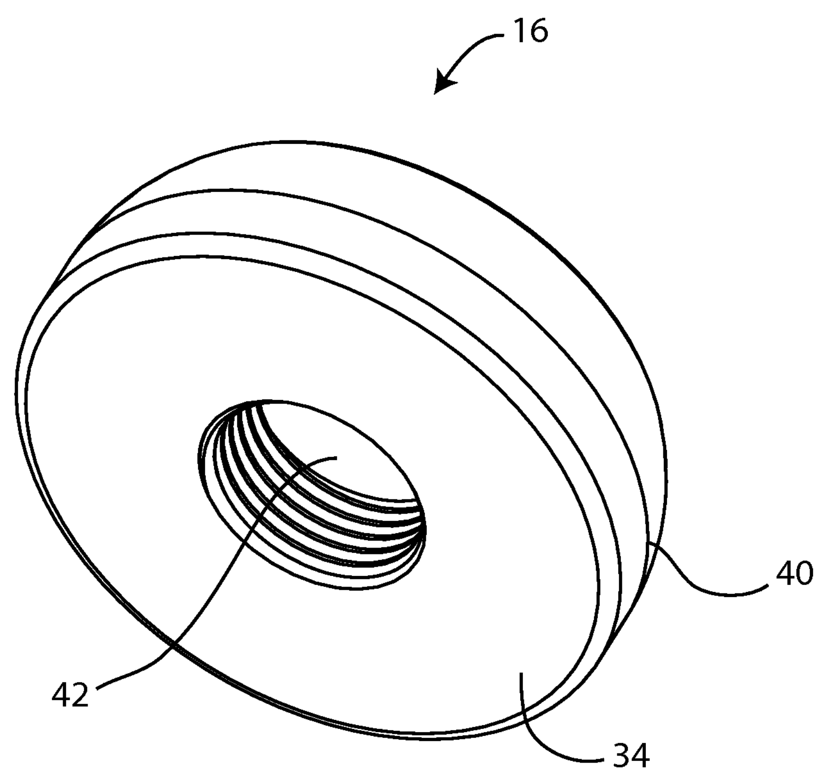
FIG. 8 is a perspective view of the head of FIG. 1.
Figure 9:
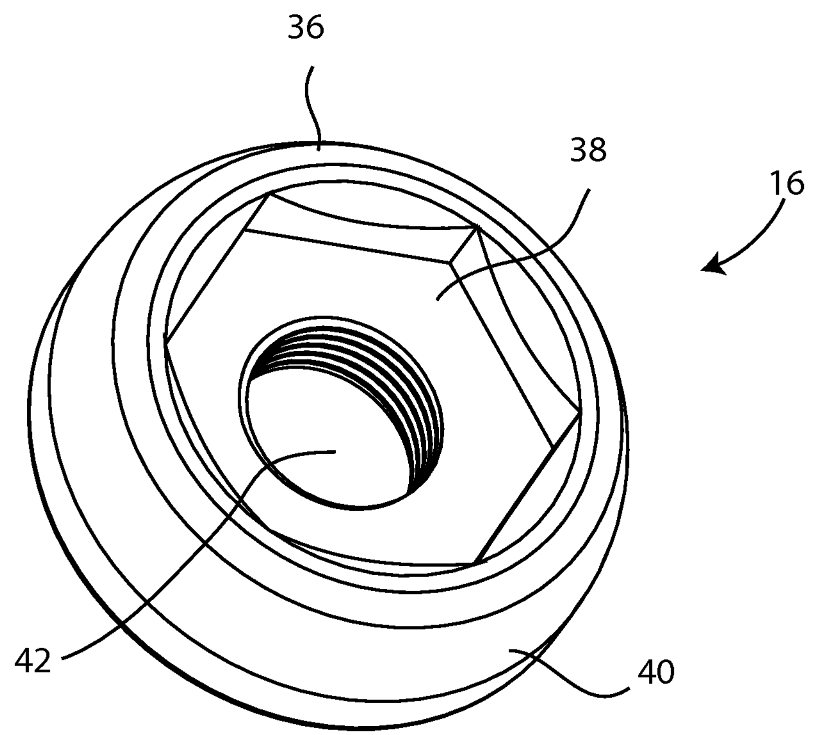
FIG. 9 is an alternate perspective view of the head of FIG. 8.
Figure 10:
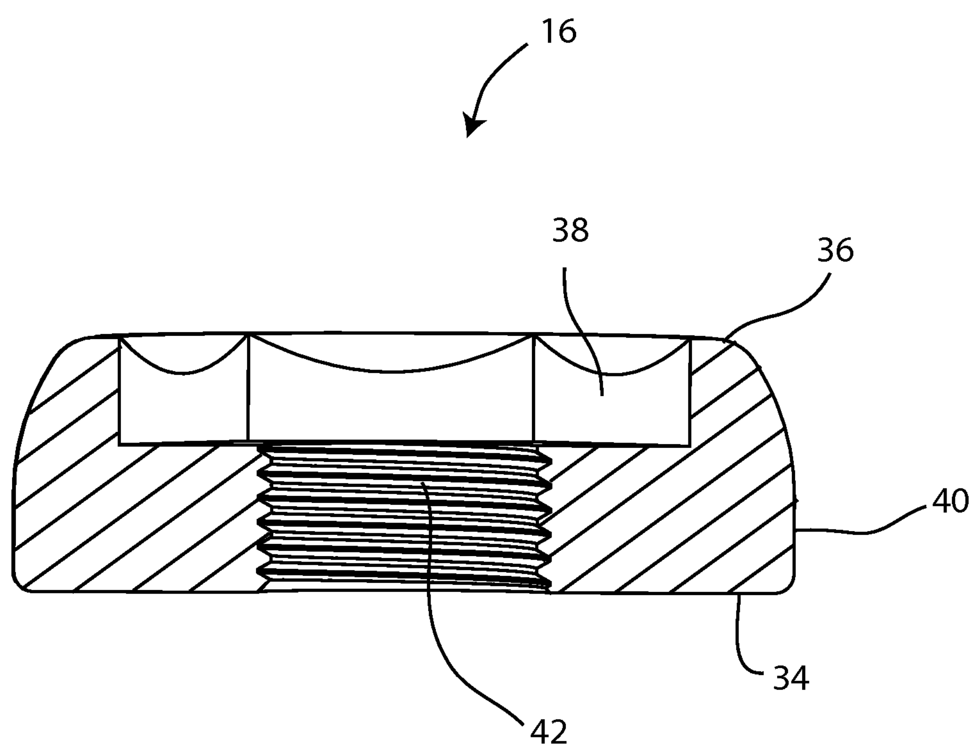
FIG. 10 is a cross sectional side view of the base of FIG. 8.

Referring to FIGS. 8-10, the head 16 may be somewhat disc shaped and includes a second spring engagement surface 34, or lower surface, wherein the lower surface 34 may be flat to allow the springs 18 to easily engage the head 16. The disc shape of the head 16 may have a greater height than that of the base 14. A circumferential wall 40 may extend from the lower surface 34 to a top surface 36 which may be slightly rounded or convex. The top surface 36 may include a void 38 extending at least partially into the body of the head 16 toward the lower surface 34. The void 38 may be hexagonal in shape but may take on any polygonal shape configured to receive an insertion, installation or tightening instrument. The head 16 may also include a second aperture 42, which may be central to the head, and substantially cylindrical. The second aperture 42 may extend through the entire body of the head 16 and may be threaded to engage the threads on the proximal end 13 of the shaft 12. However the second aperture 42 may be tapered or smooth or may include ridges or barbs to engage an appropriate fit with the proximal end 13 of the shaft 12.

The diameter of the head 16 may be substantially similar to the diameter of the base 14. The second aperture 42 diameter may be substantially similar to the diameter of the first aperture 30 and sufficient to engage the proximal end 13 of the shaft 12 in an appropriate manner either through threads, taper, barbs, ridges of the like either by threaded fit, snap fit, press fit or other means known in the art.

The head 16 may reversibly engage, by way of threading, press fit or other means, the proximal end 13 of the shaft or may non-reversibly engage, by way of welding or other means, the proximal end 13 depending on the engagement features. In the case of a taper or ridged engagement of the head 16 to the proximal end 13 it may engage by way of a snap fit or press fit or the like. Upon insertion of the head 16 onto proximal end 13 or upon engagement of the head 16 to the proximal end 13 the second aperture 42 may be coaxial with the longitudinal axis of the shaft 12.

Figure 11:
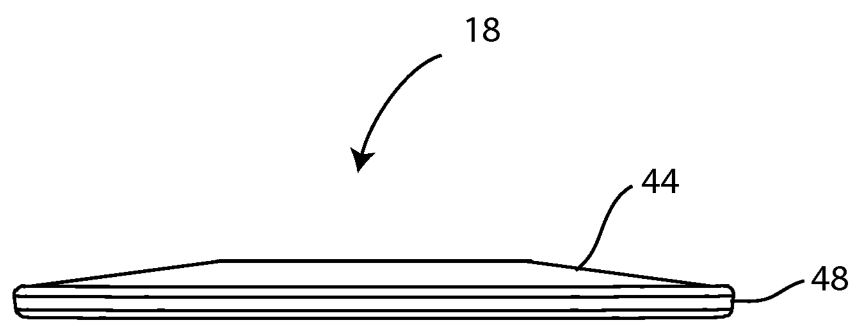
FIG. 11 is a perspective view of the spring of FIG. 1.
Figure 12:
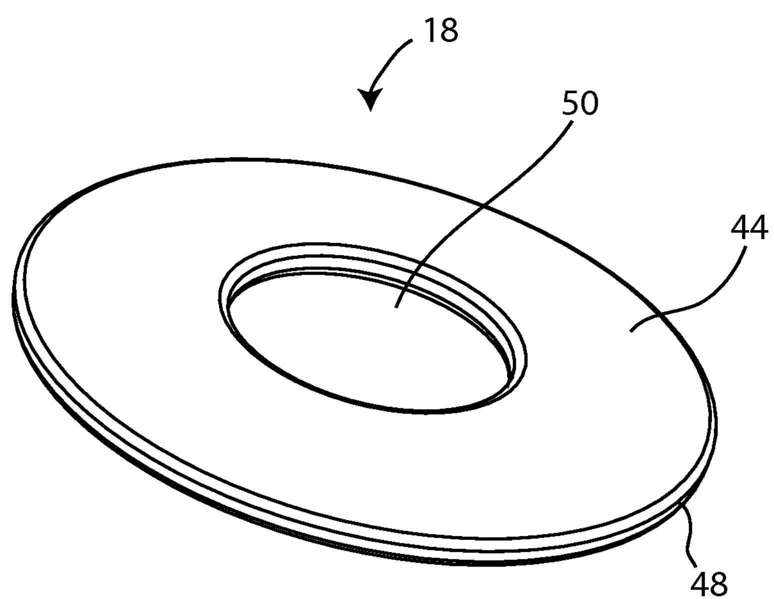
FIG. 12 is a side view of the spring of FIG. 11.
Figure 13:
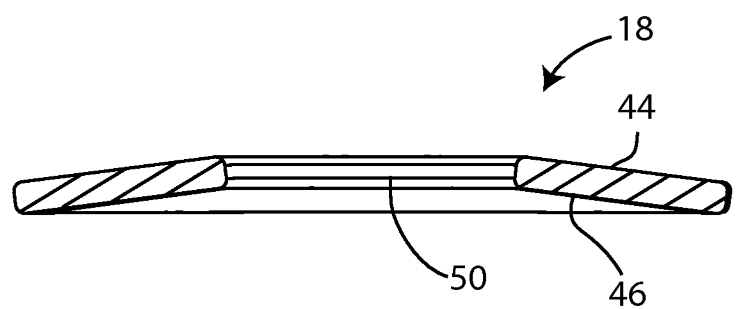
FIG. 13 is a cross sectional side view of the spring of FIG. 11.

Referring to FIGS. 11-13, a spring 18 may be substantially disc shaped with a convex first portion 44 and a concave second portion 46. The convex first portion 44 may be on the upper side of the spring 18 and the concave second portion 46 may be on the lower side of the spring 18. The first portion 44 and second portion 46 may be defined by a circumferential spring wall 48. The shape of the spring and the concave and convex features are what provide the spring 18 compression by allowing the spring 18 to be manipulated to apply compression on the system 10. From a side view, the spring 18 may be somewhat trapezoidal in shape. The spring 18 may be a Belleville washer with the capacity to deliver compression to the system 10. The spring 18 may be combined with a plurality of springs 18 to effect interfragmentary gap reduction from natural resorption during healing, and maintain load sufficient to stabilize the fracture zone while avoiding pressure necrosis in a seated screw. It will compensate during the natural osteoclastic resorption by retraction without the loss of force necessary to continue promotion of bone growth.

Referring to FIG. 12-13, the spring 18 may further include a third aperture 50, which may be central to the spring 18, which may extend through the entire body of the spring 18. Upon insertion of the spring 18 onto proximal end 13 or upon engagement of the spring 18 to the proximal end 13, the third aperture 50 may be coaxial with the longitudinal axis of the shaft 12. Multiple springs 18 (see FIGS. 1-3) may be stacked on top of each other to provide greater compressive force in the system 10 and reduced screw loosening after the screw 10 is placed in a bone. The number and orientation of the springs may vary depending on the compressional force need. For example, the height of the spring stack may be as low as 2.5 mm on a nominal 3 mm diameter screw and provide adequate compression.

The diameter of the spring 18 may be substantially similar to the diameter of the head 16 and the base 14. The third aperture 50 diameter may be substantially similar to the diameter of the first aperture 30 or second aperture and sufficient to slidably engage the proximal end 13 of the shaft 12.

The installation of springs 18 from a proximal end prior to head installation enables springs 18 to maintain a small aperture 50 which may only be slightly larger than the shaft 12. The small aperture allows for increased spring compression and flexibility relative to springs with larger apertures required by traditional installation of spring washers over bone threads of distal portion 22. It is appreciated that the spring 18 may have an outside diameter no larger than that of the head 16.

Assembly of the system 10 also allows for the relative small diameter of the third aperture 50 to the outside diameter of the washer 18 which allows for greater compressive strength and flexibility of the system 10. Assembly of the system 10 (and the other embodiments disclosed herein) may be done during operation to obtain different levels of compression or may be preassembled. One method of assembly may include sliding a threaded portion (disclosed in more detail herein) on to the shaft 12 from the proximal end 13 and being freely slidable along the shaft 12 from the distal portion 22 being unable to pass the distal portion because of the radially extending threads 24. The base 14 may then slide onto the shaft from the proximal end 13 and also freely slide along the shaft 12 until engaging the threaded portion. The spring 18, which may include a varying number of washers, may then slide onto the shaft, the washers 18 being inserted onto the shaft in either the same directions or in alternating directions, or half in a first direction and half in a second direction. The washers may freely slide until engaging the base 14. Finally a head 16 engages the shaft in any of the manners previously disclosed, threads, press fit, snap fit and prevents withdraw of the threaded portion, base 14 and spring 18. The slidable portions, upon insertion into bone, may all engage one another and sit adjacent to one another when fully engaged in the bone.

When the plurality of springs 18 are engaged with the system 10 the springs 18 may all face the same direction, thus providing complementary fit of the convex portions with the concave portions, with the concave portions facing the base 14. However, the plurality of springs 18 may also be placed half in one direction—convex portion facing the base 14—and half in the opposite direction—convex portion facing the head 16—creating a spring void 219 (refer to FIG. 17) between the two halves of the plurality of springs because of two concave portions facing one another. Alternatively the springs 18 may alternate in their assembly with convex portions adjacent to one another and concave portions adjacent to one another.

Figure 14:
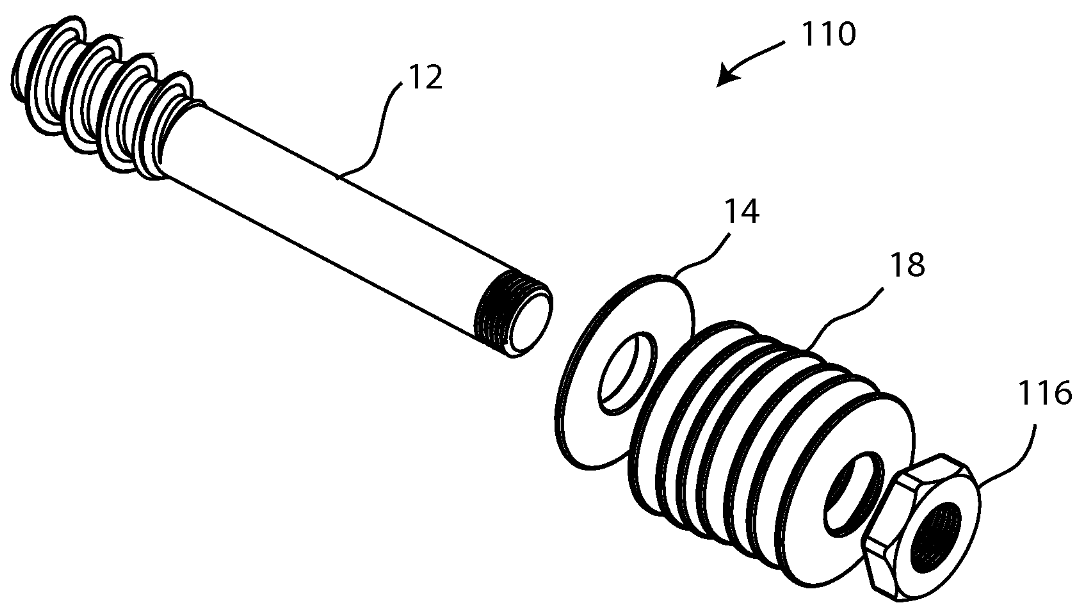
FIG. 14 is a perspective view of an alternate embodiment of a system with the base, the shaft, and the springs of FIG. 1 with an alternate head.

Referring to FIG. 14, an alternate embodiment of the system 110 illustrates substantially similar features to the previous disclosed embodiment. An alternate embodiment head 116 is different than the previously disclosed head 16 in that the alternate embodiment head 116 may be substantially hexagonal in shape. It will be appreciated that many alternate embodiments are possible for the shape and size of the base 14 and that of springs 18 of proximal portion 20 in pursuit of better approximating contours of the external dimensional envelope of traditional screw heads while enabling the advantages of spring action for sustained force. This may include a smaller outside diameter of base 14 and springs 18 that vary in outside diameter, thickness and spring height. The stack of springs 18 may vary from being smaller outside diameter near the base 14 to a larger outside diameter as they reside closer to the upper portion of the spring stack 18.

Figure 15:
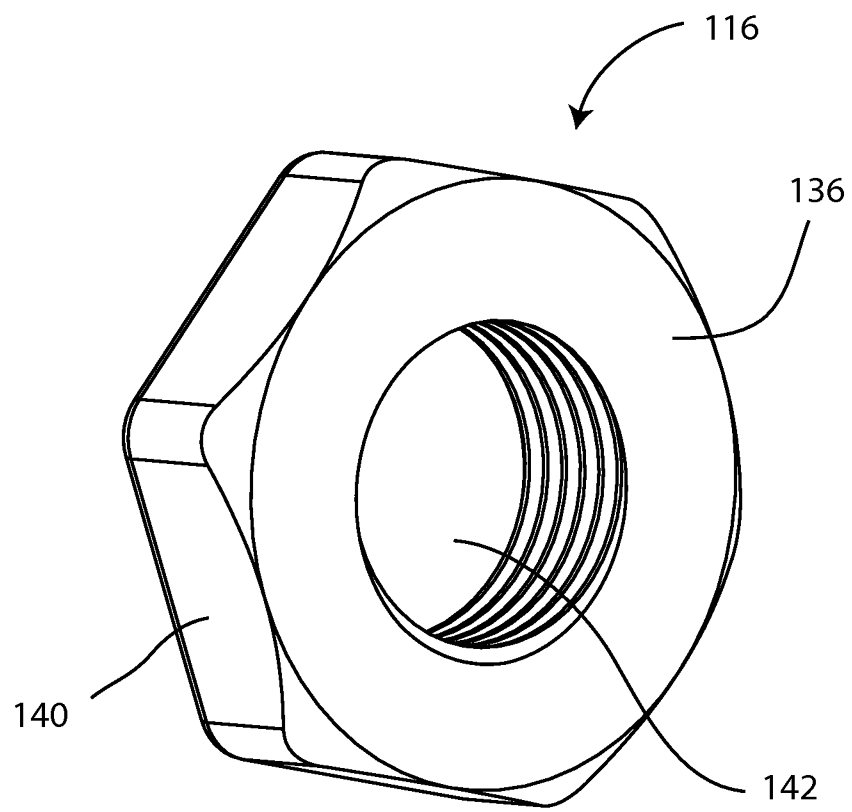
FIG. 15 is a perspective view of an alternate embodiment of a head of FIG. 14.
Figure 16:
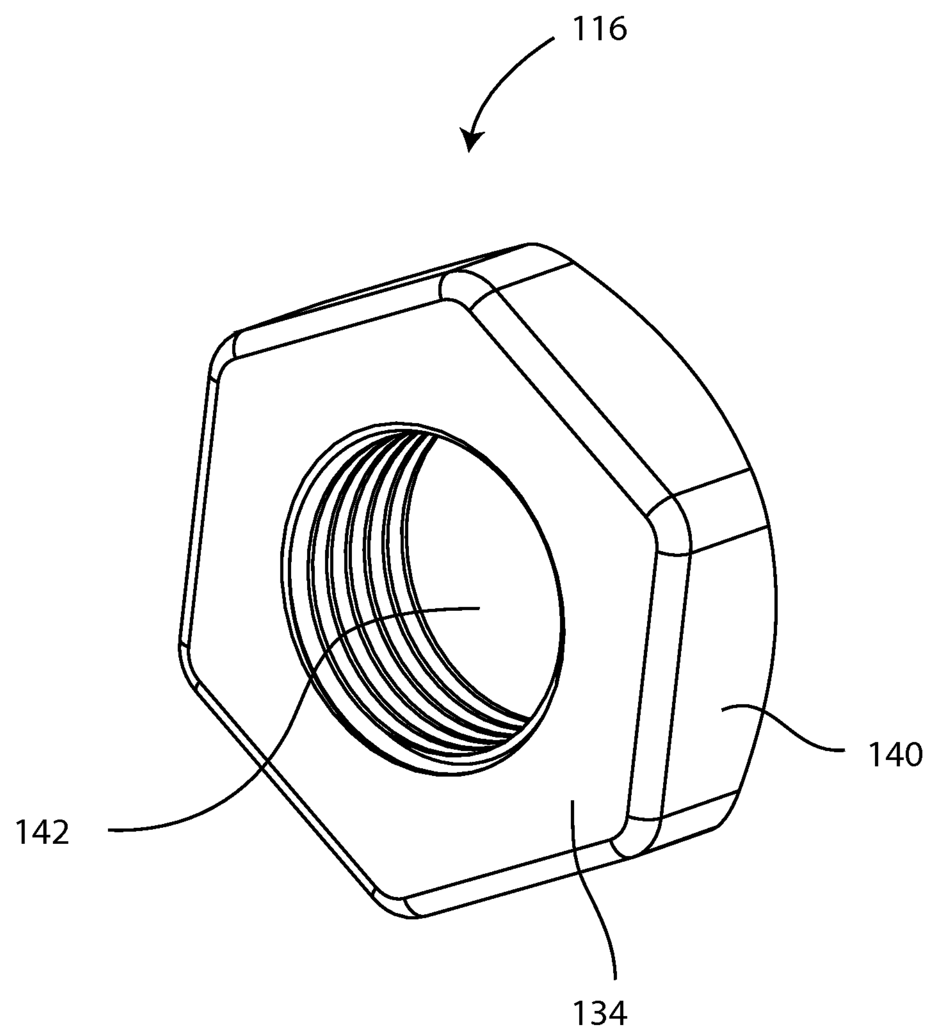
FIG. 16 is an alternate perspective view of the head of FIG. 15.

Referring to FIGS. 15 and 16, the head 116 may include a circumferential wall 140 substantially hexagonal in shape from a top view. The wall 140 may extend from a lower surface 134 to a top surface 136. The lower surface 134 is configured to engage the springs 18 of the system 110 and may be flat. The top surface 136 may be relatively smooth and somewhat convex or rounded extending form the wall 140 toward the top surface 136. A bore 142 may extend entirely through the body of the head 116 from a lower surface 134 and a top surface 136. The bore 142 may be central to the head 116 and may include thread extending the length of the bore 142. The diameter of the head 116 may be smaller than the diameter of the springs 18 and/or the base 14. However, the diameter of the bore 142 may be substantially similar to the diameter of the first aperture 30 and second aperture 42 and sufficient to engage the proximal end 13 of the shaft 12 in an appropriate manner either through threads, taper, barbs, ridges or the like either by threaded fit, snap fit, press fit or other means known in the art.

It will be appreciated that the bore may not include threads and may alternatively be tapered, comprise ridges or barbs or similar engagement features to engage an appropriate fit with the same or similar, and perhaps complementary, features of the proximal end 13 of the shaft 12. Upon insertion of the head 116 onto proximal end 13 or upon engagement of the head 116 to the proximal end 13 the bore 142 may be coaxial with the longitudinal axis of the shaft 12.

Figure 17:
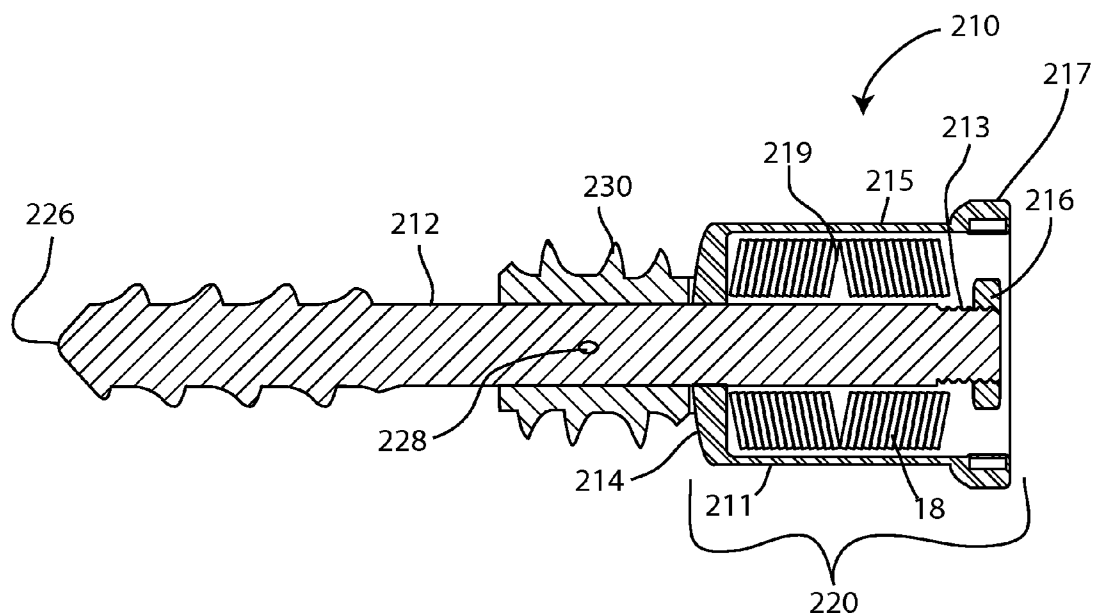
FIG. 17 is a cross-sectional side view of an alternate embodiment screw with a cup-like component with a springs, or washers, in a non-compressed position.
Figure 18:
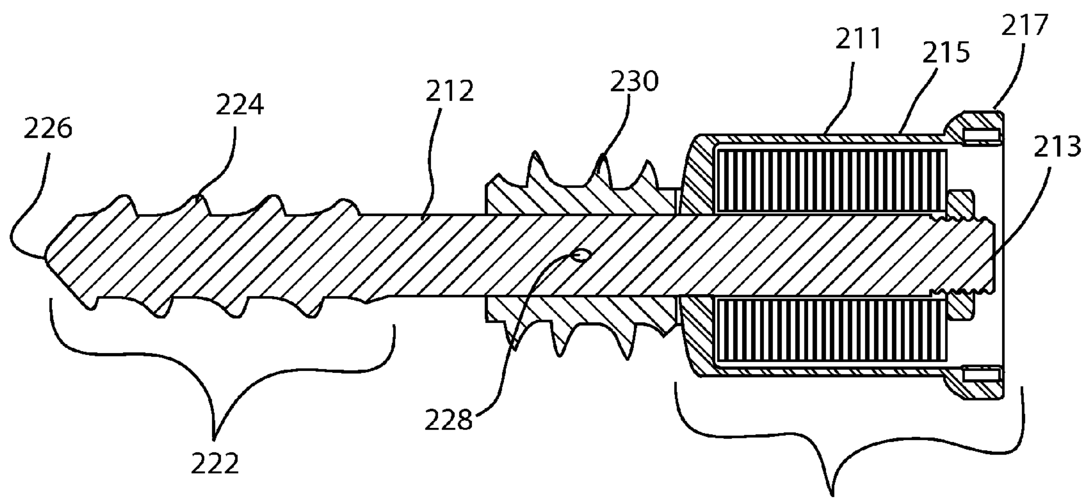
FIG. 18 is a cross-sectional side view of the screw of FIG. 17 with the springs in a compressed position.

Referring to FIGS. 17-18, an alternate embodiment of a system 210 or screw includes a cup 211 with a head 216, which may be similar to the previous hexagonal head 116, springs 18, or washers, a shaft 212 with a proximal portion 220 and distal portion 222. Referring to FIG. 17, the cup 211 may slidably engage the shaft 212 and be manufactured or machined separately from the screw 210 all-together. The cup 211 includes a base 214 radially extending from the shaft 212 and the cup 211 may include a central bore for allowing the shaft 212 to pass through. The cup 211 includes a radially and longitudinally extending wall 215 extending from the base 214 toward the proximal end 213. The cup 211 may include a radial lip 217, or flange, at the proximal end of the cup 211.

The head 216 may engage the proximal end 213 of the shaft 212 by means previously described herein for alternate embodiments. As shown in FIG. 17, the head 216 may threadably engage the proximal end 213. As the head 216 advances distally the head may compress the washers 18 thus eliminating the spring void 219 created, as described in paragraph [0077], compressing the springs 18 and tensioning the screw 210.

Referring to FIG. 17, the springs 18 may be retained by the cup 211 by slidably engaging the shaft 212 through the third aperture 50. The springs may rest on the base 214 of the cup 211. As previously described the springs may alternate in their engagement in the manner described in paragraph [0077].

The distal portion 222 of the shaft 212 may include threads 224. A distal tip 226 of the shaft 212 may be a sharp, pointed tip and may be self-tapping. However, it will be appreciated that the distal tip 226 may also be a blunt end similar to the previous embodiments described herein. Distal to the cup, a threaded portion 230 may slidably engage the shaft 212 and may slide freely along the shaft between the threads 224 and the base 214 of the cup 211 until engaged in the bone. The threaded portion 224 may have threads which extend radially from a central axis and the longitudinal axis of the shaft 212. The threads of the threaded portion 230 may have greater diameter than the threads 224 of the distal portion 222.

The cup may transfer load from a tall stack of washers that may extend below the cortical bone to bear on cortical bone under the lip at the top of the cup 211. Also, the interior surface of the cup top lip 217 may include a hexagonal shape for installation of threaded portion 230, which may be bonded or integrally formed with the cup 211 bottom. The threaded portion 230 may add head bearing capacity in cancellous bone.

As is the case with all the embodiments disclosed herein, an electronic chip with a radio frequency tag 228 may be positioned within the body of the shaft 212.

The previously described embodiments cause continuous compression between the near and far cortex of an osteotomy site. It allows for continued stability via compression, during weight bearing, tensions, moments and shears. The screw 10,110 provides dynamic compression continuously during the bone healing phases which begins immediately upon fixation and can take weeks, to several months, to years to fully complete.

The screw 10,110 is designed with the spring for initial installation at a high load with relaxation from natural resorption such that the bone state is in the compressive stress range for mechanically stabilizing the joint while facilitating osteogenic stimulation of limited intermittent mechanical loading—avoiding excessive rigidity. The configuration can be fine-tuned to achieve total micro stretch required by all sources of bone resorption at max combined stress. Thickness, stack, orientation and deflection limiters of the current device can be varied in this new construct to resist tension, shear, and torsion, which is more efficient delivering and sustaining value per unit of bone purchase.

Spring screws stretch or shorten under tension or compression respectively. The amount varies according to the screw configuration, its material properties, the load, the screw orientation in bone, and the bone properties. The amount is usually a few microns. But, due to the differential stiffness of the resisting bone, the stretching can be significant and redistribute induced load, effectively concentrating it to produce the progressive failure mode described previously. By cutting in the wedge shaped gap above threads when tapping bone to receive a screw, a more uniformly distributed load can be achieved. By engaging the full bone bearing thread 24 simultaneously, significantly larger pull out values can be achieved relative to specific bone purchase.

The screw 10 components described, work in balance or harmony together and with the body's natural reaction to optimize bone healing, often enabling the body to shorten or skip usual phases of healing. Together the elements facilitate installation at higher compressive forces, relative to its bone purchase, and dynamically close the fracture zone or interfragmentary gap as it resorbs during the first few hours to days after rigid fixation, due to osteoclastic resorption. Fixation is dynamically retained, hospitable to osteoblastic formation for sustained bone growth. The screw 10, 110 may not loosen, but may relax, calibrated for natural resorption such that the Belleville washer springs 18 in the relaxed state produce bone compression in the ideal zone for mechanically stabilizing the joint while facilitating osteogenic stimulation by limited intermittent mechanical loading—avoiding excessive rigidity while restraining movement in the fractured joint—reducing attendant delay, or failure to heal.

An osteotomy or fracture placed under the dynamic stabilizing forces of the disclosed device, allows earlier motion and weight bearing typical of earlier therapy and use—eliminating considerable muscle and bone atrophy, and loss of work time. Substantially reduced or eliminated will be post-surgery, non-weight-bearing status, as well as possibly related non-compliance for extended periods of time.

Manufacture of the device may be accomplished by specific diameter spring washers, which may be in the range of 4 mm to 10 mm, being stamped or milled from heat treated and or cold worked stainless steel using dies milled from similar material. Other components can be fabricated by rolling round wires or bars, or milling. Press fitting, threaded and micro-welding assembly may also be used.

Radio frequency tags may be used on an electronic chip and strain gauge with power provided by a magnetic induction reception coil excited by externally induced magnetic flux in close proximity to the installed tag. A hole is drilled in the spring shaft or cable anchor where the tag is inserted and anchored into place.

A surgeon may use the device to reduce the fractures or osteotomy site(s), whereupon the location for fixation screws, wire-cables, connections, bone plates, and buttons would be identified. Screw locations would be drilled, measured with a depth gauge and tapped and recessed to accommodate the selected screws. The fully assembled screws would be threaded into the tap-threaded and recessed holes and secured finger tight or to specified torsion or direct shank tension.

The sequence of screw, cable and other hardware installation and tensioning may be pre-determined. Accordingly, screw anchor hardware would be tensioned by rotating the screw head 16,116. Tensioning would proceed until proper toque is achieved to indicate design tension has been achieved in the shaft 12 and springs 18, or until the reading from the radio frequency tag-strain gauges indicates the predetermined proper tension has been achieved, whereupon, further tensioning would cease. Following multiple hardware installations, actual tension reading is again verified with the strain gauges and adjustments made, whereupon, the site would be surgically closed. The radio frequency tag-strain gauges transmit strain readings when energized, at predetermined intervals. Upon follow-up doctor visits, the stored data from the externally worn energizer and recorder is reviewed and thereby continuing tension levels verified. Automatic transmission via cell phone technology may also be utilized. Warning and transmission can be triggered by strain gauge sensing of strain above or below quality standards.

If necessary, the site can be reopened and the screws retightened or removed. The radio frequency tag-strain gauges could be deactivated permanently when they are no longer needed.

Figure 19:
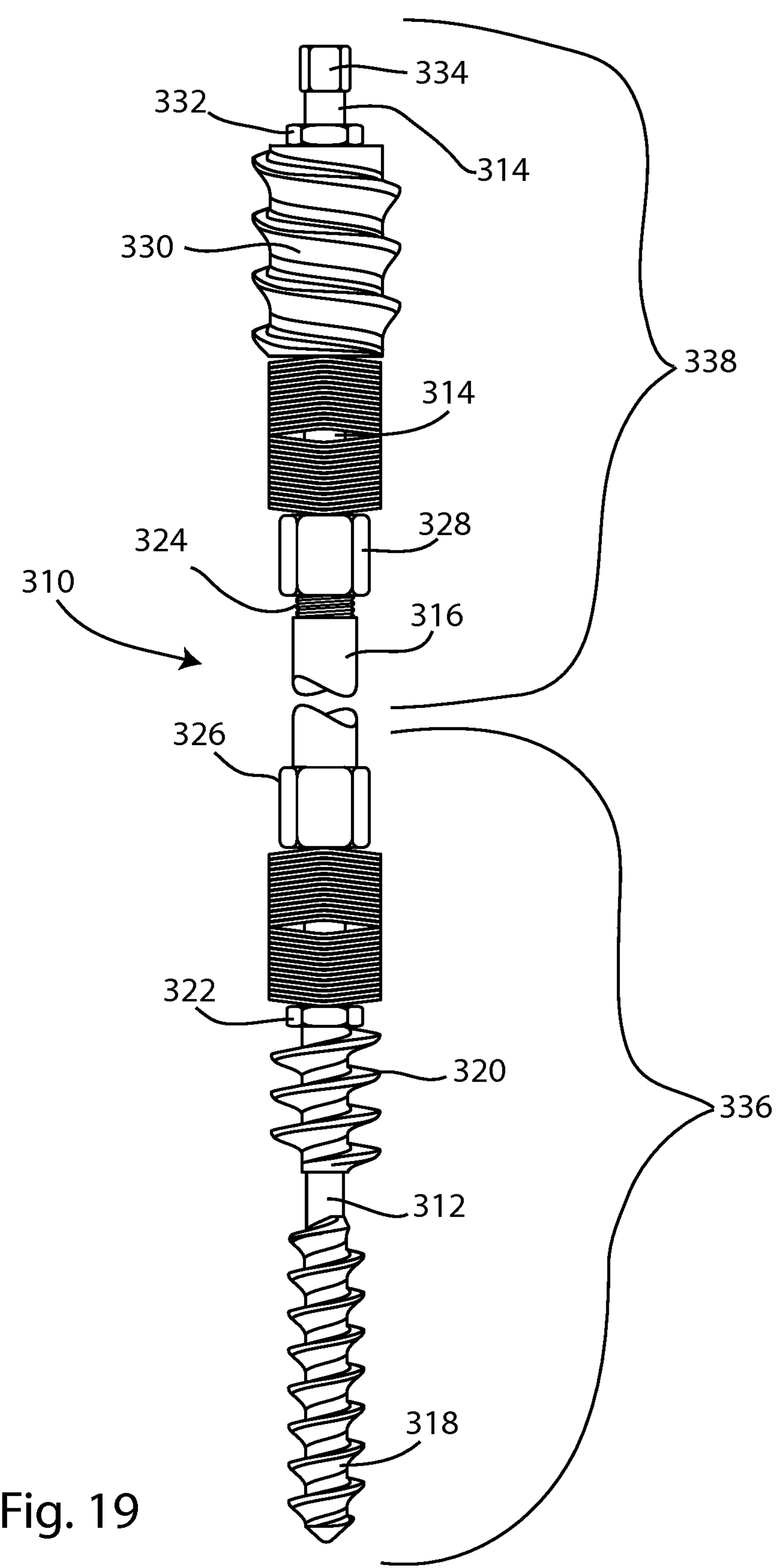
FIG. 19 is a side view of an alternate embodiment system, or screw, which may be specific to calcaneal repairs.
Figure 20:
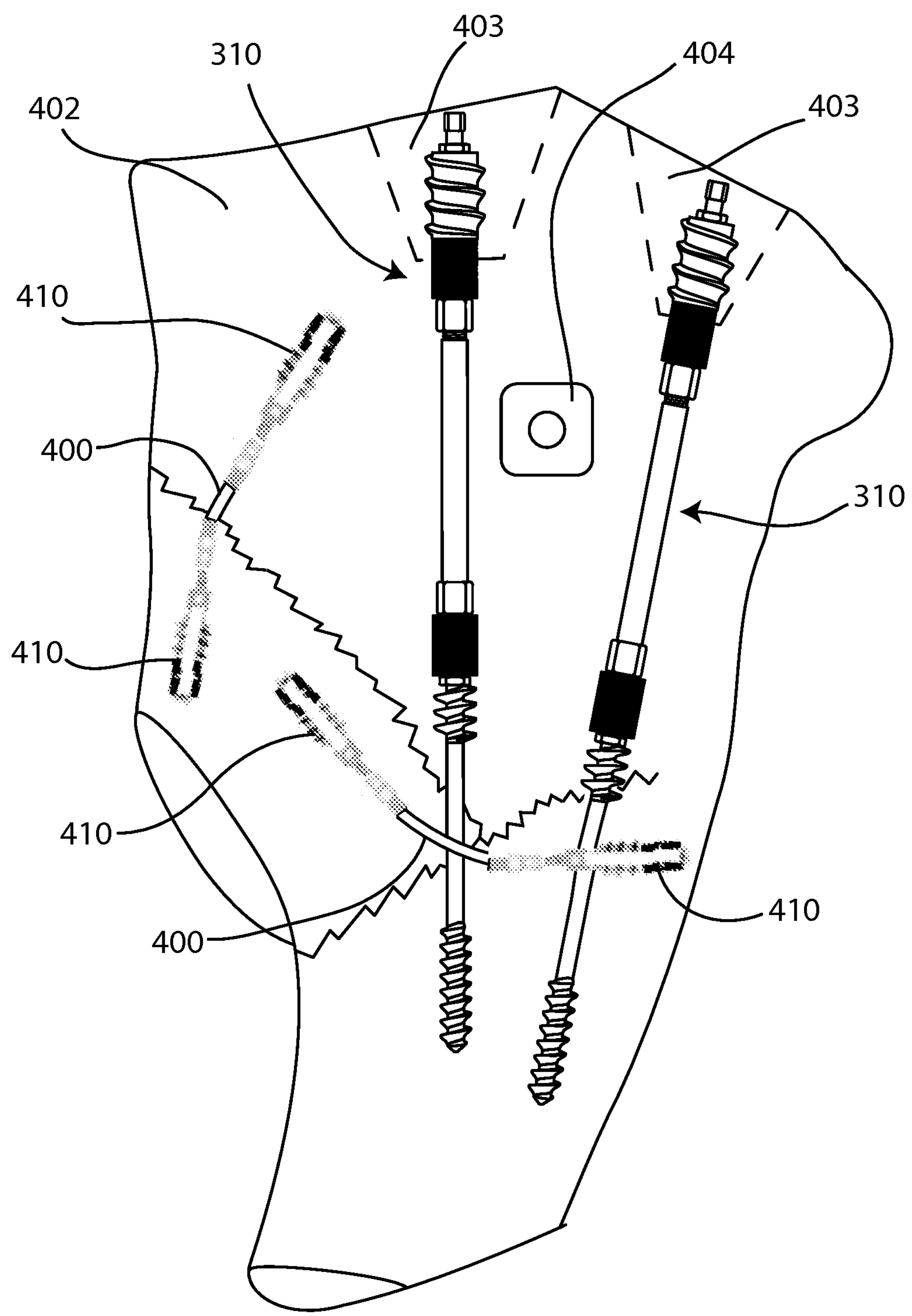
FIG. 20 is a side view of a fractured calcaneus with wire cables and the system of FIG. 19.

Referring to FIGS. 19 and 20, an alternate embodiment may include two or more components which allow for compression and tension. This embodiment may be ideal for calcaneal fractures and is described further herein.

A system 310, or screw, may include two components or portions, a first portion 336, or lower portion, which allows for bone compression, similar to the proximal portions 20 of the previous embodiment, system 10, and a second portion 338, or upper portion which allows for tensioning and stretching the calcaneus bone to reestablish proper bone dimensions. The system 310 includes a first shaft 312, a second shaft 314 and a compression rod 316. The first shaft 312 may comprise a first bone threaded portion 318 toward a distal end, the threads being aggressive enough to engage and secure the screw 310 in its appropriate location. A second bone threaded portion 320 spaced from the first threaded portion 318 may have more aggressive threads and may have a larger diameter than the first threaded portion to engage a softer portion of a bone. The second bone threaded portion 320 may be a separate piece, integral with base 322 and freely slideable along the first shaft 312. A base 322 may engage the shaft proximal the second threaded portion 320 and is configured to allow the springs 18, or Belleville washers, to rest on the base 322, and to use for removal of the system if required. The base 322 may be similar to those previously described or may be a bearing nut. A third threaded portion, may be positioned at a proximal end of the first shaft 312 and configured to engage the first shaft screw head 326 which is distal the compression rod 316, wherein the first shaft screw head may be integral to the compression rod 316 and engages the first shaft 312 by complementary threads in the first shaft screw head 326.

A proximal end of the compression rod 316 may comprise rod threads 324 to engage a compression rod head 328, which may be a head nut. The head nut 328 may include complementary threads to engage the threads of the proximal end of the compression rod 316. The compression rod head 328 engages, or may be integrally formed with, the second shaft 314.

Proximal to the compression rod head 328, the second shaft 314 allows for springs 18, to rest on the compression rod head. Proximal to the springs 18, a fourth threaded portion 330 is positioned, which may have a larger diameter then either the first 318 or second 320 threaded portions, and is sized with sufficient thread purchase to secure stability in the soft interior bone of a calcaneus or other bone. The fourth threaded portion 330 may be separate from the second shaft 314 and may be freely slideable along the second shaft. The fourth threaded portion 330, or intermediate component, is mounted to, or slides on, the second shaft 314 and is secured by a securing nut 332, which may be integral with and may be hexagonal in shape but any polygonal shape will do. A complementary void in the third threaded portion 330 may be positioned at its proximal end to slidably receive the securing nut 332.

Positioned at a proximal end of the second shaft 314, and the proximal end of the system 310, may be an installation nut 334 provided to install the entire system 310. The installation nut 334 may be hexagonal in shape but any polygonal shape is contemplated. The lower portion 336 of the system 310 may be engaged by clockwise rotation and the upper section 338 by counterclockwise rotation. It will be appreciated that the lengths of each of the first shaft 312, second shaft 314 and compression rods 316 may all vary in length and diameter; however the second shaft 314 preferably has a single length with variations in the first shaft 312 and compression rod 316 being more common.

Referring to FIG. 20, the system 310 (multiple) is depicted within a bone 402, which may be a calcaneus bone, with multiple fractures. The advantages of the screw 310 in conjunction with bone-compression producing wires 400 are to allow for fixation in a minimally invasive method. On at least one end, and maybe on both ends, of the wires 400, is a screw 410. Furthermore another medial-lateral device 404, which may be a screw of wire cable assembly, may be used for securement of the fracture in a medial-lateral direction. Further depicted in FIG. 20 are zones of compression 403, directed toward the bone exterior. These zones of compression 403 may require an internal head, rather than an external head.

Surgery for calcaneal fractures is ideally performed within the first 6-8 hours following injury, before significant edema sets in. If this cannot be accomplished in this time frame, the surgery is usually prolonged for 7-10 days until the edema subsides enough to allow for skin closure.

The screw 310 has two components that will allow for compression of the distal portions while also providing an extension element proximally. This would ideally hold the fractures in a compressed environment to encourage healing while holding the bone out to the anatomic length as is achieved with existing art by a buttress plate. The bone-compression producing wires 400 can be placed laterally to medially to hold the posterior facet fragments and/or the calcaneocuboid articulation together while also being placed at other locations to reduce the width and correct the varus component. These wires 400 and screws 310 can be placed percutaneously which will reduce the need for the larger lateral extensile approach as well as reduce the need to prolong surgery until edema reduces.

Figure 21A:
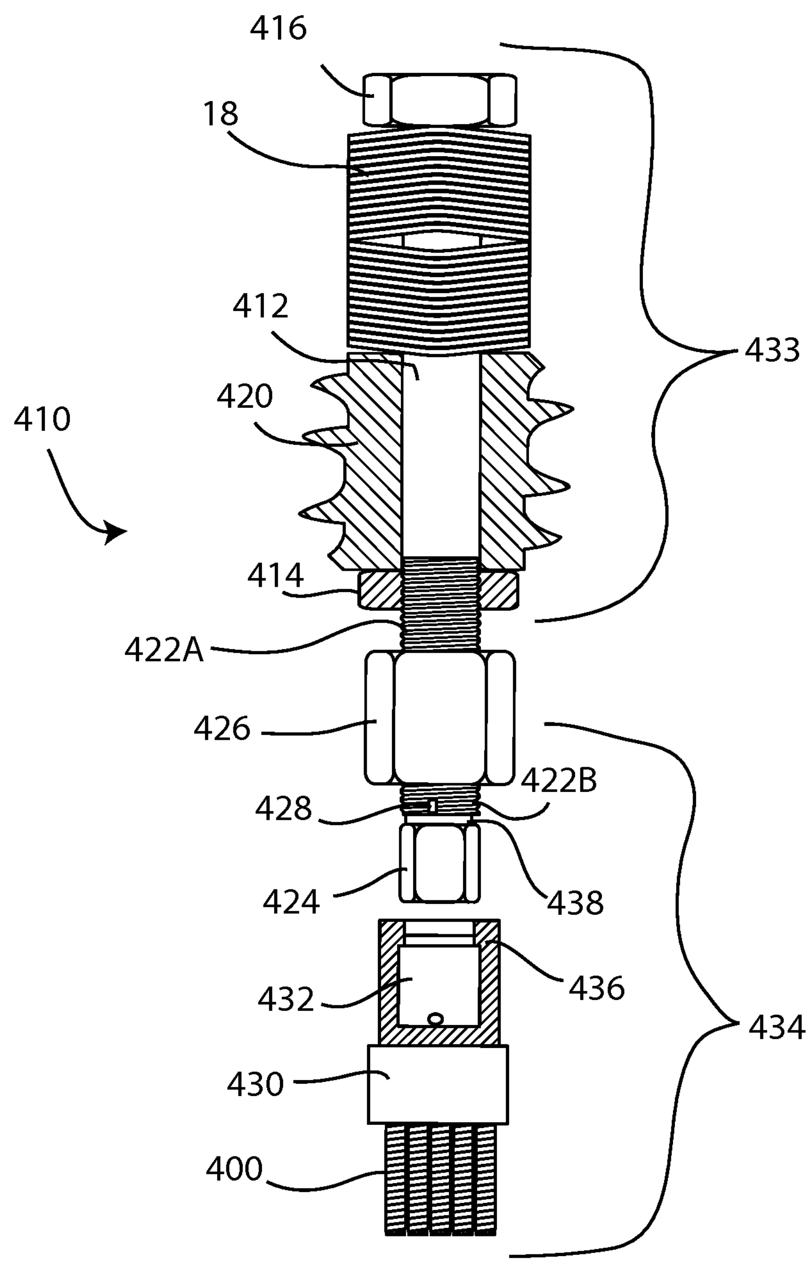
FIG. 21A is a partial cross-sectioned side view of a cable-screw system with the wire cables of FIG. 20 with the cable system dis-engaged with the screw system.
Figure 21B:
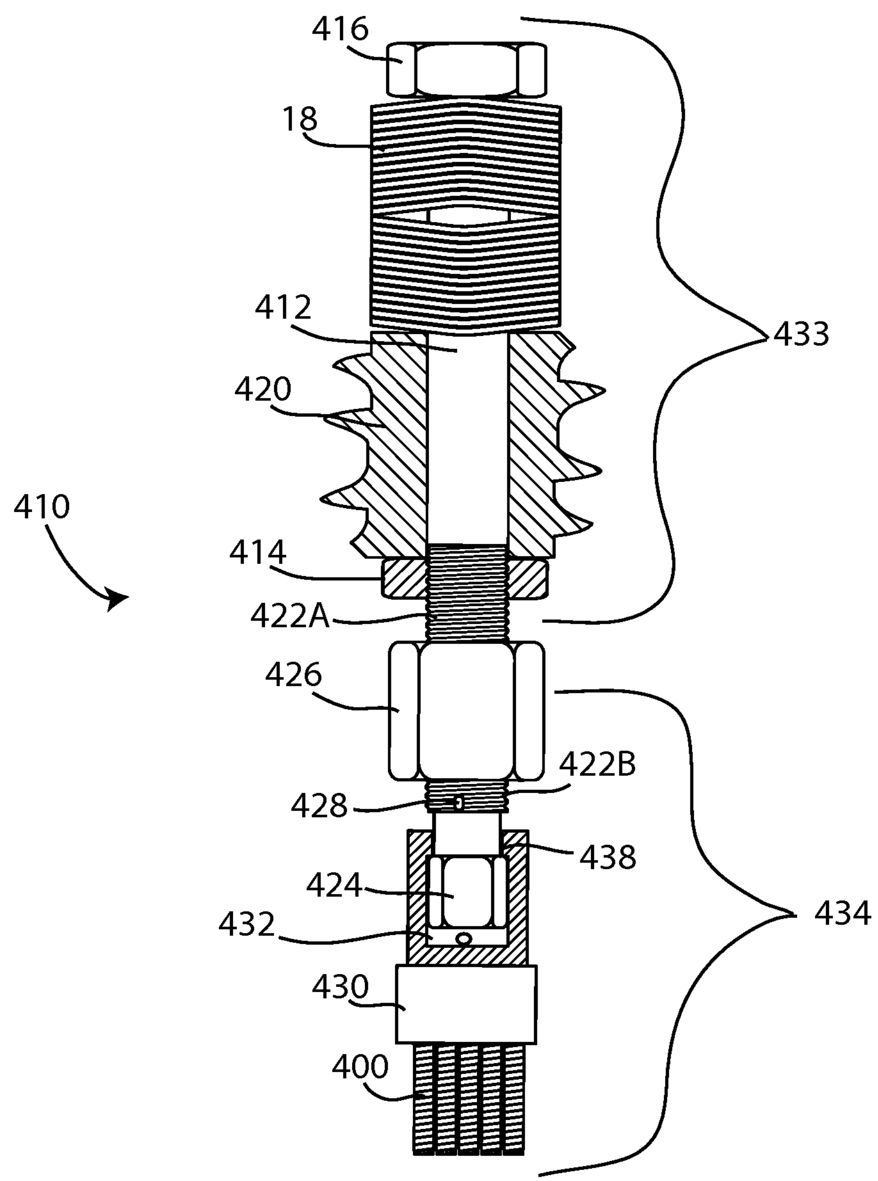
FIG. 21B is a partial cross-sectioned side view of a cable-screw system with the wire cables of FIG. 21A with the cable system engaged with the screw system.

An alternate embodiment of a system 410 is depicted in FIGS. 21A and 21B with the compression producing wires 400 (which are further described later herein). A spring and head portion 433 may be positioned proximal a wire cable portion 434 and connected via a socket nut 424 and tensioned by a coupling nut 426 which will be described further herein.

Similar to a portion of the screw 310 previously described herein, the system 410 includes a shaft 412, a base 414 integral with a bone threaded portion 420, springs 18 proximal to the base 414, a head 416 integral with the shaft 412 and proximal to the springs 18. The base 414 is hexagonal shaped and integral with the bone threaded portion 420 and only slideably engages shaft 412, including only slidably engaging threads 422A and 422B. It is anticipated that rotating base 414 will rotationally install bone threaded portion 420, and thereby the head and spring or the head and no spring portion 433. This installation is preparatory to being connected to the cable 400 via the wire cable portion 434 and tensioned by rotating coupling nut 426. Similar to previous embodiments, the shaft 412 of the system 310 comprises a longitudinally extending cylindrical body with a longitudinal axis. A distal end of the shaft 412 may comprise a hexagonal or other polygonal nut 424 and distal threads 422 just proximal and adjacent to the nut 424. The base 414 and bone threaded portion 420 may slidably engage the shaft 412 by sliding onto the shaft 12 at the distal end. The springs 18 may also slidably engage the shaft 412 by sliding onto the shaft 412 at the distal end. The shaft 412 may include a non-threaded portion between the distal threads 422 and the proximal head 416.

The bone threaded portion 420, integral with the base 414 may slidably engage the shaft 412 and move freely along the shaft until engaging springs 18. The bone threaded portion 420 may be positioned proximal to and integral with the base 414 and distal the springs 18 and the head 416, proximal the springs 18. Alternatively the springs 18 may be eliminated and the head 416 may be positioned just proximal the bone threaded portion 420 integral with the head 414 to create a head and no spring portion positioned proximal the wire cable portion 434 and connected via a socket nut 424 and tensioned by a coupling nut 426 which will be described further herein. The separate threaded portion 420 may have a larger radial footprint than any of the base 414, head 416, or springs 18, and with larger threads to engage the bone.

Distal to the base 414 are the distal threads 422*a* of the spring and head portion 433 and proximal threads 422*b* of the wire cable portion 434. Threaded between the distal threads 422*a* and proximal threads 422*b* may be a coupling nut 426 with interior right and left hand threads. The distal thread 422*a* and proximal threads 422*b* may be oppositely threaded on either side of the coupling nut 426 to couple the right and left hand threads of 422*a*, and 422*b* respectively, and together allow for advancement and tensioning of the system 410. An electronic chip 428 with radio frequency tags may be positioned or embedded with the shaft of the proximal threads 422*b* and will allow a user or surgeon to determine the tension in the shaft 412 as previously described.

The distal threads 422*b* may be integrally formed with a component 424, a nut connection member, which may be hexagonal in shape and configured to engage a nut receiving portion 432, or box securement portion, of the wire cable portion 434. The nut receiving portion 432 may comprise a complementary fit within a cylindrical outer wall of the wire cable portion; however any geometric cross-sectional shape of the outer wall may suffice. The nut receiving portion 432 receiving the nut connection member 424 may be preassembled or assembled during operation. The nut receiving portion 432 within the outer wall may include a shoulder 436 to engage a proximal end 438 of the nut connection member 424 to prevent withdraw of the nut connection member 424 from the nut receiving portion 432.

Distal to, and integrally formed with the nut receiving portion, is a cable crimp 430 which may be configured to secure the cable(s) 400 to the system 410 via the nut receiving portion 432 to the connection member 424 and thus to the proximal threads 422*b* of the wire cable portion 434 via the coupling nut 426 coupling the wire cable portion 434 to the spring and head portion 433. Crimping of the cable(s) 400 to the cable crimp 430 may be accomplished by any means known in the art.

Figure 21C:
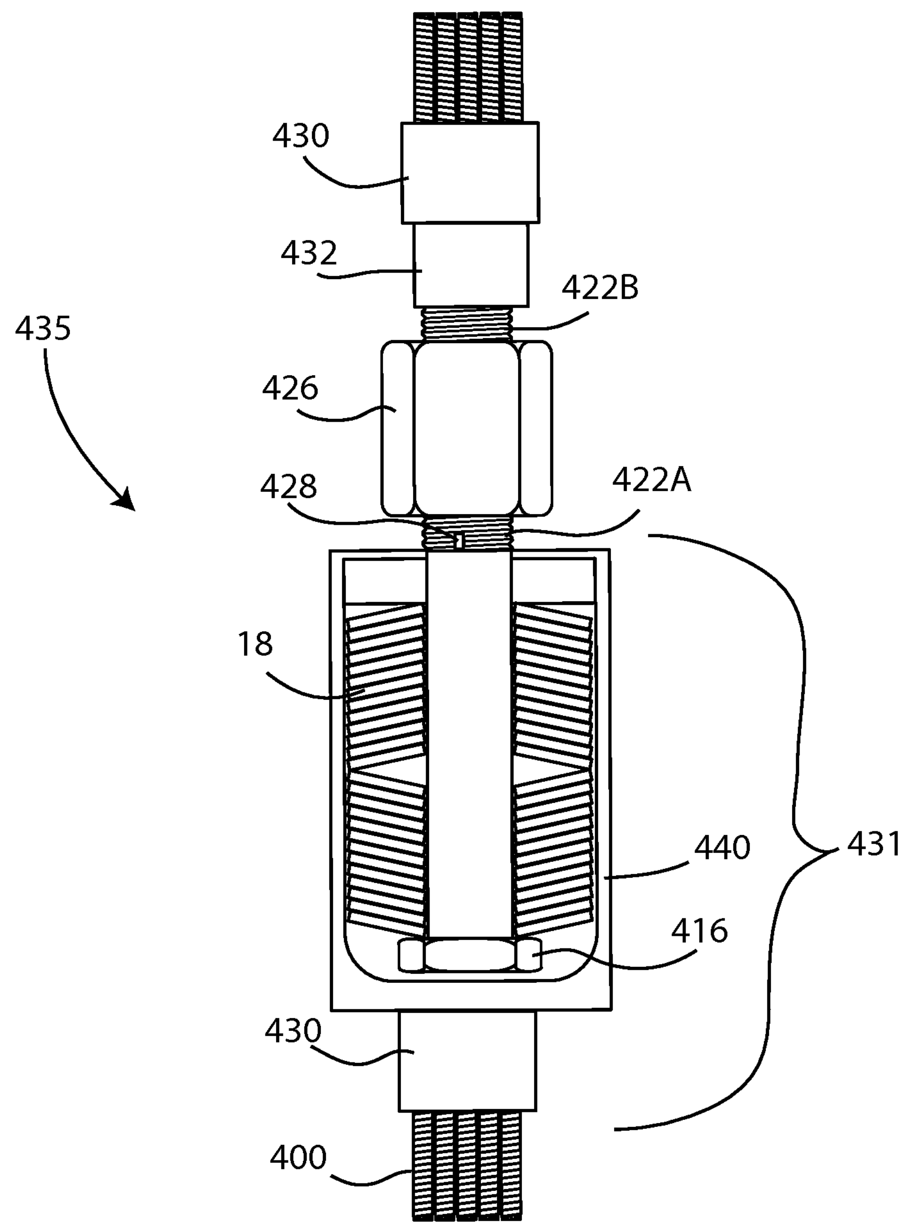
FIG. 21C is a side view of an alternate embodiment of a wire cable system with two cable systems, one with springs and one without springs.

It will be appreciated that the system 410 is modular and may be manipulated in a variety of ways. For example referring to FIG. 21*b* a cable anchor may not include a spring section 18. For another example, referring to FIG. 21C, a tensioning portion 431 may include, at its proximal end, an assembly similar to that of the wire cable portion 434 including a cable crimp 430 engaging, or integrally formed with, a spring or washer cage 440, with cables extending from the crimp 430. This alternate assembly may allow for a cable to encircle bone and attach to itself via the system 435 and provide cable tension and thereby circumferential bone compression. Longitudinal and circumferential compression may be combined and general fracture zone stability may be provided as desired (refer to FIG. 24). Longitudinal bone compression and structural stability may be provided by a combination of cables and a spring and head portion 433 with anchor systems 410 on one end FIG. 21A and a head without a spring portion anchor systems 410 on the other end FIG. 21B. Alternatively the a longitudinal cable may be anchored on both ends by anchor systems 410, each with spring and head portion 433 with the integrally formed cable crimp 430 on each anchor system 410 with each spring and head portion 433 engaging the cable between one another via the coupling nuts 426 as previously described.

Figure 21D:
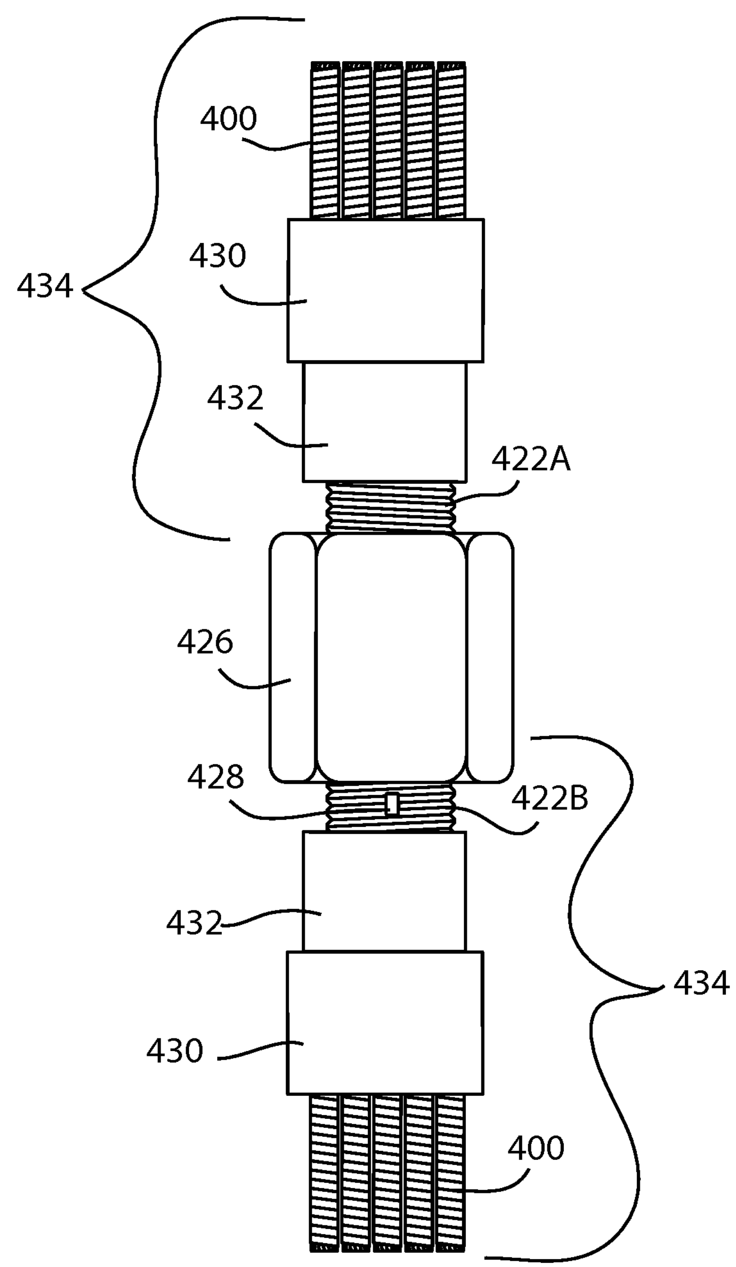
FIG. 21D is a side view of a wire cable system with two cable systems connected together.

Another alternate assembly embodiment may include two wire cable portions 434 coupled together via the coupling nut 426. Referring to FIG. 21D, the assembly may essentially comprise two cable crimps 430 crimping cable(s) 400 and two nut receiving portions 432 with two nut connection members 424 with two proximal threaded portions 422A, 422B coupled together via the coupling nut 426. When used in conjunction with other and alternate systems disclosed herein (refer to FIG. 24), this assembly may allow for a stable, minimally invasive, tensioned structure encircling the fractured bone that anatomically retains and three dimensionally compresses fractured bone fragments. Friction is induced between the compressed, fractured bone fragments, creating with the tensioned structure a composite, stable shear and moment resisting system. Proper bone dimensions are retained and stabile resistance to internal and external forces are enabled during the surgery to install it. The springs in the system sustain bone stability and compression, optimal for healing throughout the process.

Figure 22:
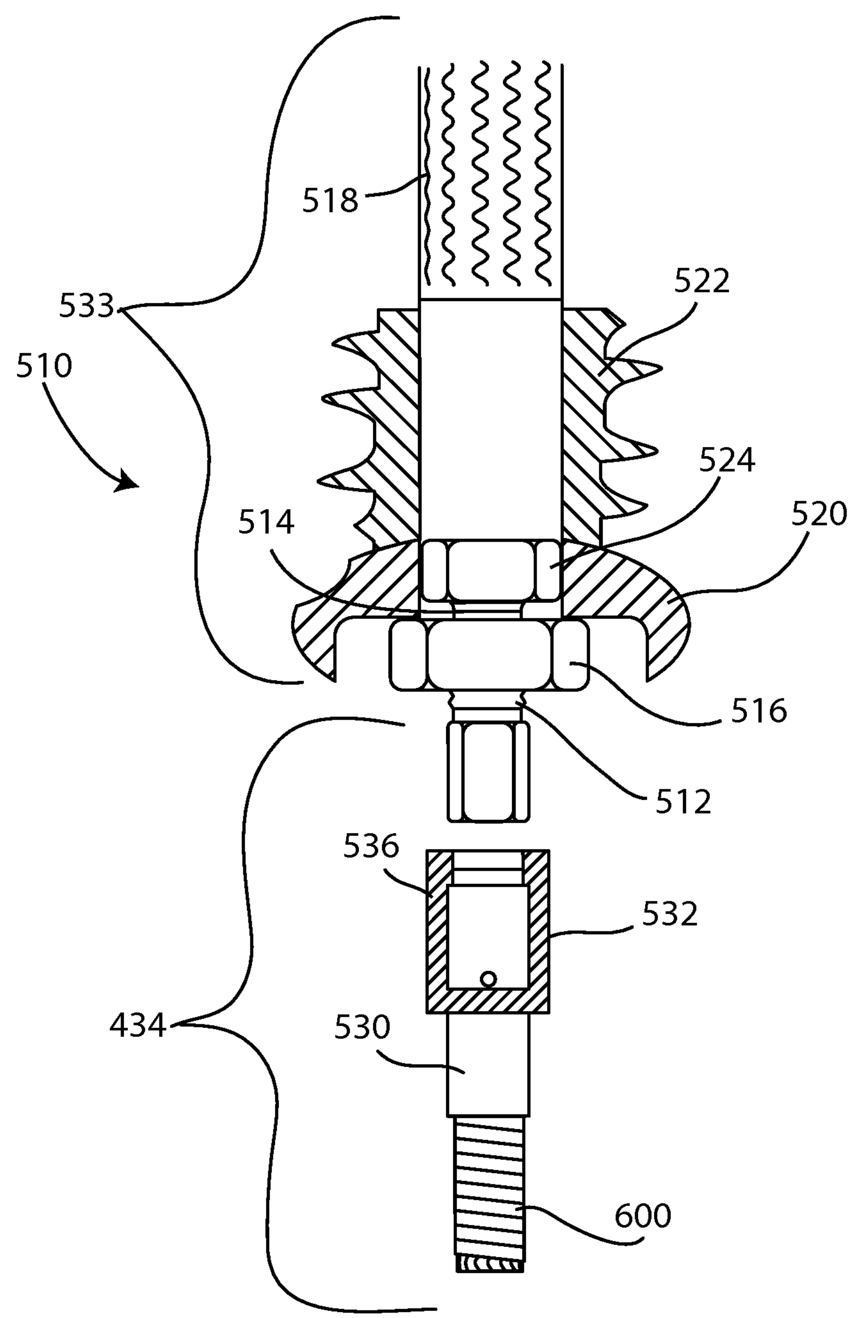
FIG. 22 is a partially cross-sectioned side view of an alternate embodiment of the cable-screw system of FIG. 21.

Referring to FIG. 22, an alternate embodiment of a system 510 is illustrated. With many of the components similar to previously described embodiments system 510 may use different springs 518 than those springs 18, Belleville washers, as previously described but it will be appreciated that the springs 518 may be Belleville washers as well. While the illustrated embodiment depicts a wire cable portion 434 engaged with a spring and head portion 533 it will be appreciated that the spring and head portion 533 may be stand alone and function similar to the previous spring and head portion 433 embodiments. Different than the previous embodiments a head 516 may be similar to the coupling nut 426 to engage the spring and head portion 533 with a wire cable portion 534. The spring and head portion 533 includes a first shaft 512 extending away from the wire cable portion 434, the shaft 512 including a longitudinal axis. A separate second shaft 514 with threads extends from a nut 524 where the second shaft may threadably engage the head 516 similar to the distal threads 422*a* of the previous embodiment. The nut 524 may be integrally formed with the first shaft 512 or may separately sit within the shaft 512 and non-rotatably engage the shaft 512.

At a proximal end of the shaft may reside a shaft head 520 which may extend radially from the shaft 512 forming a circumferential shoulder and bulbous head which may at least partially encircle the head 516 within the shaft head 520. Positioned distal the shaft head 520 may be a threaded portion 522 which may slidably engage the shaft 512 and is freely slidable along the shaft from the shaft head to distal threads (not shown, but which may resemble previously disclosed screw threads). Alternate springs 518 may be used to provide bone compression and may extend longitudinally along the shaft body. The wire cable spring 518 may perform the same or similar function as the previously disclosed springs 18, Belleville washers. Many different wire cable springs are contemplated including fine spring wire cable, with helical coiled spring sleeve, or a spring wire cable with rectangular strands.

Referring back to FIG. 22, the system 510 may closely depict the wire cable assembly shown in FIG. 20 with the wire cable(s) 400 extending between two screws. The screws may be that spring and head portion 533 as depicted here; however the screws may also be the assemblies of the previous systems alternatively engaging the wire cable portion 434 in a similar manner.

The wire cable portion 434 is substantially similar to the previously disclosed embodiment with the exception of a differing cable(s) 600 extending from a wire crimp 530 which may be different from the previous embodiment because of a possible different wire assembly being used. Differing wire assemblies are disclosed further herein. The wire crimp 530 may be smaller circumferentially depending on the wire configuration desired. Similarly a nut 536 engages a nut receiving member 532 in much the same manner as the previously disclosed embodiment. Further the nut receiving member 532 is integrally formed with the wire crimp 530; however, in this embodiment the nut receiving member may be circumferentially larger than the wire crimp 530, again depending on the wire configuration desired.

Figure 23:
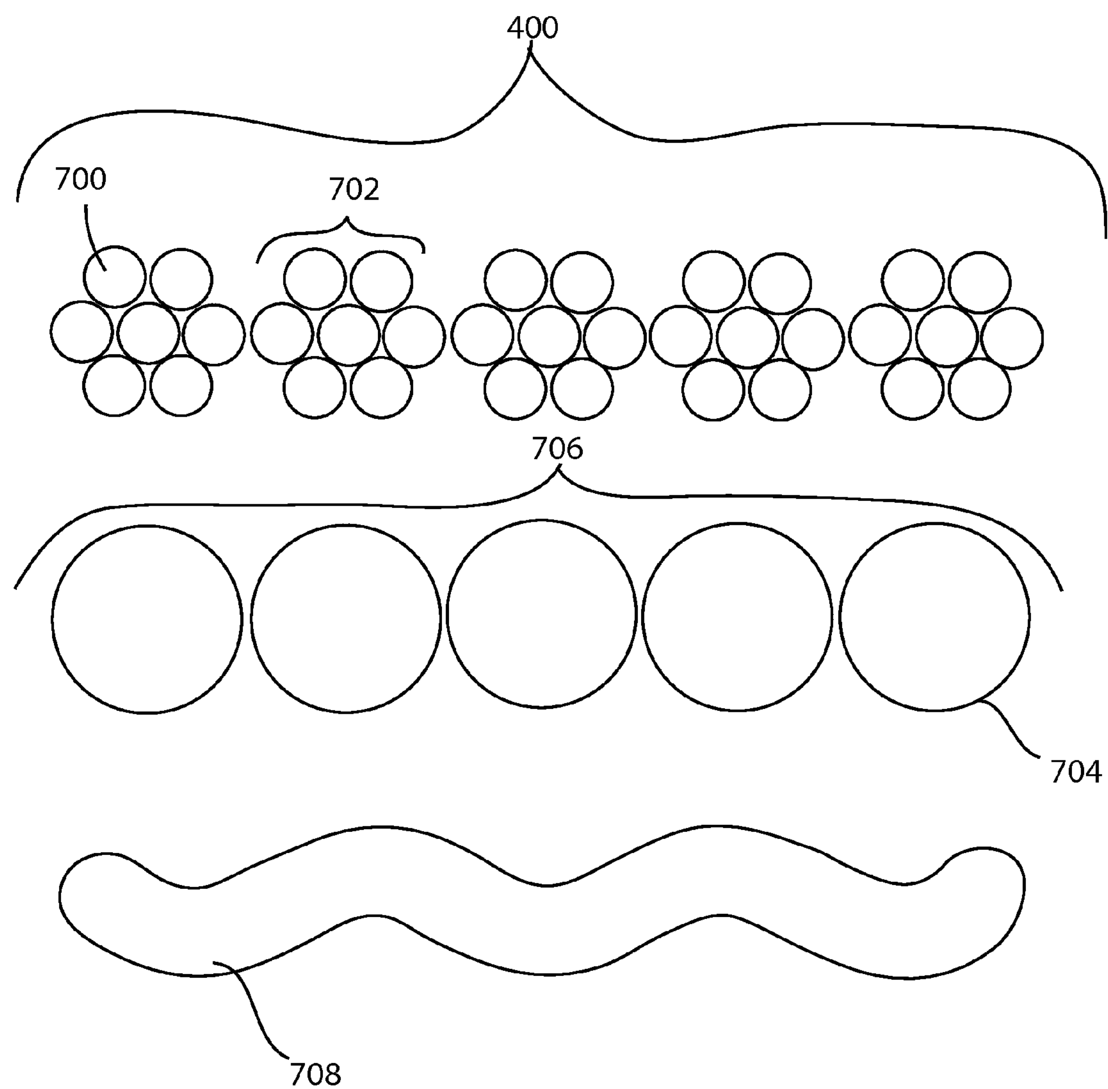
FIG. 23 is a cross section view of a cable system of FIG. 20.

Different wire configurations are depicted in FIG. 23. A first wire 700 is shown, which may be a twisted wire strand. Multiple first wires 700 may be combined to form a wire strand 702 and woven into a flat wire cable 400 and depicted as disclosed previously. The wire cable(s) 400 are smaller wires in a flat cable profile and provide additional bearing surface to allow for greater load on the bone over a larger bearing surface causing less stress at single points on the bone. Individual larger wires 704 may be placed in a flat multi-wire cable configuration 706 as well. Another possible wire configuration is a wavy plate cable configuration 708 which may reduce costs and evenly spread the load in a cost-effective way.

It will be appreciated that the device and alternate embodiments herein have been contemplated for use as a stand-alone device; however it is anticipated that the device may also be used in bone plates, in conjunction with external fixation rigs, in spine applications as well as osteoporotic bone.

Figure 24:
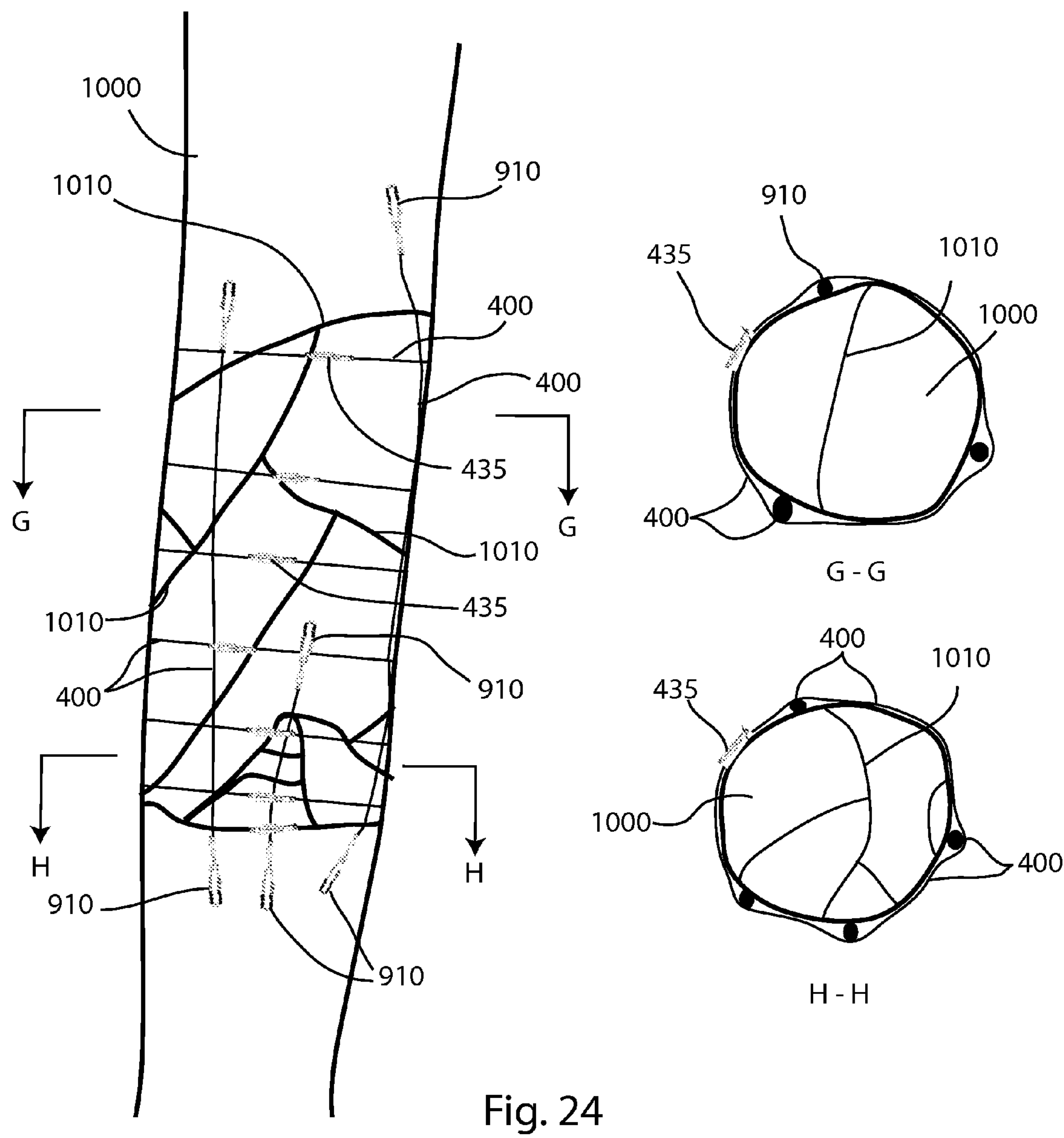
FIG. 24 is a side view of multiple cable wire or cable screw systems of FIGS. 21 and 22, engaging a fractured bone.

Referring to FIG. 24, a cable system assembly is illustrated across a multiple fracture 1010 bone 1000 with multiple cross sections. Multiple screws or systems may be used to stabilize the fracture in a longitudinal direction along with multiple wire cable assemblies to circumferentially surround the fractured bone by using cable attachment assemblies as previously disclosed for alternate systems 410. The screws 910 that may be used may be any of the previously disclosed embodiments, 410, engaged with the cable(s) 400. The use of multiple longitudinal constructs with compression screws 910 using cable(s) 400, combined with circumferential cable systems 410, using cable(s) 400 provide for an immediate stable, minimally invasive, tensioned composite structure of the fractured bone leading to shorter recovery time and even immediate weight bearing.

The components disclosed herein may be made from titanium, stainless steel, or cobalt chrome. Other contemplates materials include graphite fiber reinforced non-biodegradable plastics to achieve reduced bone purchase, metals, polymers, ceramics, glasses, composite materials, biological materials or tissues, or other biocompatible materials. Different materials may be used for individual components. Different materials may be combined in a single component.

It should be understood that the present system, kits, apparatuses, and methods are not intended to be limited to the particular forms disclosed. Rather, they are to cover all combinations, modifications, equivalents, and alternatives falling within the scope of the claims.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

The invention claimed is:

1. A system comprising:
- a first portion and a second portion proximal to the first portion;
- wherein the first portion comprises a first shaft extending between a first proximal portion and a first distal portion;
- wherein the first proximal portion comprises a first base that slides freely over the first shaft and a first head fixed to the first shaft proximal to the first base, wherein first spring is between the first base and the first head, wherein the first base and the first head each have a spring engaging surface;
- wherein the first base and the first head each have a larger outside diameter than the first shaft;
- wherein the first base comprises a threaded bone engaging surface opposite the first base spring engaging surface;
- wherein the second portion comprises a second shaft extending between a second proximal portion and a second distal portion;
- wherein the second proximal portion comprises a second base fixed to the second shaft, an intermediate component that slides freely over the second shaft proximal to the second base, and a second head fixed to the second shaft proximal to the intermediate component, wherein a second spring is between the second base and the intermediate component, wherein the second base and the intermediate component each comprise a spring engaging surface.

2. The system of claim 1, wherein the first distal portion comprises a blunt distal tip.

3. The system of claim 1, wherein the first base comprises a bore, wherein the first base slidably engages the first shaft, the first shaft at least partially passing through the bore.

4. The system of claim 1, wherein the first base extends radially from and is freely slidable along the first shaft.

5. The system of claim 1, wherein the first spring comprises a Belleville washer.

6. The system of claim 1, wherein the first spring comprises a plurality of Belleville washers.

7. The system of claim 6, wherein the plurality of Belleville washers face the same direction.

8. The system of claim 1, wherein the first head comprises a bore configured to threadably engage a proximal end of the first shaft, the first head further comprising a polygonal shape configured to engage an insertion tool.

9. A system comprising:
- a first portion and a second portion proximal to the first portion, the first portion comprising a first shaft extending between a first proximal portion and a first distal portion;
- wherein the first proximal portion comprises a first base and a first head, wherein a first spring is between the first base and the first head, wherein the first base and the first head each have a spring engaging surface;
- wherein the first base and the first head have larger outside diameters than the first shaft; and
- wherein the second portion comprises a second shaft extending between a second proximal portion and a second distal portion, wherein the second proximal portion comprises a second base, an intermediate component proximal to the second base, and a second head, wherein a second spring is between the second base and the intermediate component, wherein the second base and the intermediate component each comprise a spring engaging surface, wherein the intermediate component slides freely over the second shaft;
- wherein the second head is proximal to the intermediate component.

10. The system of claim 9, further comprising a rod engaged with and between the first portion and the second portion.

11. The system of claim 9, wherein the intermediate component comprises external threads.

12. The system of claim 9, wherein the first and second bases each extend radially from the first and second shafts respectively and the first and second heads threadably engage the first and second shafts respectively.

13. The system of claim 9, wherein the first spring comprises a Belleville washer.

14. The system of claim 9, wherein the first spring comprises a plurality of Belleville washers.

15. The system of claim 14, wherein at least a portion of the Belleville washers face different directions.

16. The system of claim 9, wherein the first head and the second head are each hexagonal and comprise a bore configured to threadably engage proximal ends of the first and second shafts respectively.

17. A method of assembling a system comprising:
- engaging a first base to a first screw by sliding the first base onto the first screw from a proximal end of the first screw toward a distal end of the first screw, wherein the first screw comprises a first shaft extending between a first proximal portion and a first distal portion, wherein the first distal portion comprises threads extending radially from the first shaft, the first distal portion further comprising the distal end;
- engaging a first spring onto the first screw by sliding the first spring from the proximal end of the first screw toward the distal end of the first screw;
- positioning the first spring proximal to the first base;
- positioning a first head proximal to the first spring;
- fixing the first head to the proximal end of the first screw, wherein the proximal end of the first screw and the first head comprise complementary threads;
- fixing a second distal portion of a second shaft to the first proximal portion of the first shaft, wherein the second shaft extends between the second distal portion and a second proximal portion;
- fixing a second base to the second distal portion of the second shaft;
- sliding a second spring over the second shaft from the second proximal portion toward the second distal portion;
- positioning the second spring proximal to the second base;
- sliding an intermediate component over the second shaft from the second proximal portion toward the second distal portion;

positioning the intermediate component proximal to the second spring; and fixing a second head to the second proximal portion of the second shaft.

18. The method of claim 17, further comprising advancing the first base toward the distal end of the first screw, wherein the first base comprises a bore, wherein the first base slidably engages the first shaft, the first shaft at least partially passing through the bore.

19. The method of claim 18, further comprising advancing the first spring toward the distal end of the first screw until the first spring engages the first base, wherein the first spring comprises a plurality of Belleville washers.

20. The method of claim 19, further comprising advancing the first head toward the distal end of the first screw until the first head engages the first spring, wherein the first head comprises a threaded bore and the proximal end of the first screw comprises recessed external threads, wherein the threaded bore is configured to threadably engage the proximal end of the first screw.

* * * * *